US012262952B2

(12) United States Patent
Dehghani

(10) Patent No.: US 12,262,952 B2
(45) Date of Patent: Apr. 1, 2025

(54) SYSTEMS AND METHODS TO OPTIMIZE REACHABILITY, WORKSPACE, AND DEXTERITY IN MINIMALLY INVASIVE SURGERY

(71) Applicant: Activ Surgical, Inc., Boston, MA (US)

(72) Inventor: Hossein Dehghani, Boston, MA (US)

(73) Assignee: ACTIV Surgical, Inc., Boston, MA (US)

( * ) Notice: Subject to any disclaimer, the term of this patent is extended or adjusted under 35 U.S.C. 154(b) by 875 days.

(21) Appl. No.: 17/349,900

(22) Filed: Jun. 16, 2021

(65) Prior Publication Data

US 2022/0000557 A1 Jan. 6, 2022

Related U.S. Application Data

(63) Continuation of application No. PCT/US2019/068778, filed on Dec. 27, 2019.
(Continued)

(51) Int. Cl.
*A61B 34/10* (2016.01)
*A61B 34/30* (2016.01)

(52) U.S. Cl.
CPC ............. *A61B 34/10* (2016.02); *A61B 34/30* (2016.02); *A61B 2034/105* (2016.02); *A61B 2034/107* (2016.02); *A61B 2034/302* (2016.02)

(58) Field of Classification Search
CPC ... A61B 34/10; A61B 34/30; A61B 2034/105; A61B 2034/107; A61B 2034/302
See application file for complete search history.

(56) References Cited

U.S. PATENT DOCUMENTS

| 4,772,831 A | 9/1988 | Casler, Jr. et al. |
| 5,808,665 A | 9/1998 | Green |

(Continued)

FOREIGN PATENT DOCUMENTS

| EP | 2672715 A2 | 12/2013 |
| WO | WO-2010096447 A2 | 8/2010 |

(Continued)

OTHER PUBLICATIONS

Dunn, et al. Laser speckle contrast imaging in biomedical optics. Journal of Biomedical Optics 15(1), 011109 (Jan./Feb. 2010).
(Continued)

*Primary Examiner* — Kira Nguyen
(74) *Attorney, Agent, or Firm* — Cesari and McKenna, LLP

(57) ABSTRACT

Systems, methods, and computer program products for quantification of error in tool orientation of a surgical robotic are disclosed. A first robotic arm is provided where the robotic arm includes a surgical instrument and a tool disposed at the distal end of the surgical instrument. A first orientation of the tool is determined including a first x-component, a first y-component, and a first z-component. A desired orientation of the tool is determined including a second x-component, a second y-component, and a second z-component. A first angle between the first x-component and the second x-component is determined, a second angle between the first y-component and the second y-component is determined, and a third angle between the first z-component and the second z-component is determined. An error metric based on the first angle, the second angle, and the third angle is determined.

21 Claims, 16 Drawing Sheets

Related U.S. Application Data

(60) Provisional application No. 62/785,957, filed on Dec. 28, 2018.

(56) References Cited

U.S. PATENT DOCUMENTS

| | | | |
|---|---|---|---|
| 5,876,325 A | 3/1999 | Mizuno et al. | |
| 6,001,108 A | 12/1999 | Wang et al. | |
| 6,088,105 A | 7/2000 | Link | |
| 6,183,485 B1 | 2/2001 | Thomason et al. | |
| 6,206,894 B1 | 3/2001 | Thompson et al. | |
| 6,223,100 B1 | 4/2001 | Green | |
| 6,309,397 B1 | 10/2001 | Julian et al. | |
| 6,325,808 B1 | 12/2001 | Bernard et al. | |
| 6,373,963 B1 | 4/2002 | Demers et al. | |
| 6,491,702 B2 | 12/2002 | Heilbrun et al. | |
| 6,503,195 B1 | 1/2003 | Keller et al. | |
| 6,542,249 B1 | 4/2003 | Kofman et al. | |
| 6,549,288 B1 | 4/2003 | Migdal et al. | |
| 6,563,105 B2 | 5/2003 | Seibel et al. | |
| 6,564,086 B2 | 5/2003 | Marchitto et al. | |
| 6,613,041 B1 | 9/2003 | Schrunder | |
| 6,643,563 B2 | 11/2003 | Hosek et al. | |
| 6,645,196 B1 | 11/2003 | Nixon et al. | |
| 6,697,164 B1 | 2/2004 | Babayoff et al. | |
| 6,800,057 B2 | 10/2004 | Tsujita et al. | |
| 6,850,872 B1 | 2/2005 | Marschner et al. | |
| 6,873,867 B2 | 3/2005 | Vilsmeier | |
| 6,885,464 B1 | 4/2005 | Pfeiffer et al. | |
| RE38,800 E | 9/2005 | Barbour | |
| 6,965,690 B2 | 11/2005 | Matsumoto | |
| 6,977,732 B2 | 12/2005 | Chen et al. | |
| 6,987,531 B2 | 1/2006 | Kamon | |
| 7,006,236 B2 | 2/2006 | Tomasi et al. | |
| 7,068,825 B2 | 6/2006 | Rubbert et al. | |
| 7,092,107 B2 | 8/2006 | Babayoff et al. | |
| 7,099,732 B2 | 8/2006 | Geng | |
| 7,124,066 B2 | 10/2006 | Marschner et al. | |
| 7,152,024 B2 | 12/2006 | Marschner et al. | |
| 7,184,150 B2 | 2/2007 | Quadling et al. | |
| 7,200,262 B2 | 4/2007 | Sawada | |
| 7,224,384 B1 | 5/2007 | Iddan et al. | |
| 7,230,725 B2 | 6/2007 | Babayoff et al. | |
| 7,242,997 B2 | 7/2007 | Geng | |
| 7,305,110 B2 | 12/2007 | Rubbert et al. | |
| 7,313,264 B2 | 12/2007 | Crampton | |
| 7,319,529 B2 | 1/2008 | Babayoff | |
| 7,363,201 B2 | 4/2008 | Marschner et al. | |
| 7,385,708 B2 | 6/2008 | Ackerman et al. | |
| 7,433,807 B2 | 10/2008 | Marschner et al. | |
| 7,435,217 B2 | 10/2008 | Wiklof | |
| 7,450,783 B2 | 11/2008 | Talapov et al. | |
| 7,477,402 B2 | 1/2009 | Babayoff et al. | |
| 7,489,408 B2 | 2/2009 | Harding et al. | |
| 7,491,956 B2 | 2/2009 | Knoche et al. | |
| 7,492,927 B2 | 2/2009 | Marschner et al. | |
| 7,511,829 B2 | 3/2009 | Babayoff | |
| 7,522,764 B2 | 4/2009 | Schwotzer | |
| 7,577,299 B2 | 8/2009 | Kawamata et al. | |
| 7,620,209 B2 | 11/2009 | Stevick et al. | |
| 7,630,089 B2 | 12/2009 | Babayoff et al. | |
| 7,704,206 B2 | 4/2010 | Suzuki et al. | |
| 7,724,378 B2 | 5/2010 | Babayoff | |
| 7,724,932 B2 | 5/2010 | Ernst et al. | |
| 7,751,871 B2 | 7/2010 | Rubbert | |
| 7,763,841 B1 | 7/2010 | McEldowney | |
| 7,794,388 B2 | 9/2010 | Draxinger et al. | |
| 7,821,649 B2 | 10/2010 | Bendall et al. | |
| 7,854,700 B2 | 12/2010 | Orihara | |
| 7,898,651 B2 | 3/2011 | Hu et al. | |
| 7,944,569 B2 | 5/2011 | Babayoff et al. | |
| 7,951,073 B2 | 5/2011 | Freed | |
| 7,959,557 B2 | 6/2011 | Weitzner et al. | |
| 7,961,912 B2 | 6/2011 | Stevick et al. | |
| 7,967,743 B2 | 6/2011 | Ishihara | |
| 7,990,548 B2 | 8/2011 | Babayoff et al. | |
| 7,995,798 B2 | 8/2011 | Krupnik et al. | |
| 8,027,710 B1 | 9/2011 | Dannan | |
| 8,038,609 B2 | 10/2011 | Kohno et al. | |
| 8,052,636 B2 | 11/2011 | Moll et al. | |
| 8,084,753 B2 | 12/2011 | Joshi et al. | |
| 8,231,610 B2 * | 7/2012 | Jo | A61B 34/70 606/174 |
| 8,257,303 B2 | 9/2012 | Moll et al. | |
| 8,264,536 B2 | 9/2012 | McEldowney | |
| 8,279,418 B2 | 10/2012 | Yee et al. | |
| 8,280,152 B2 | 10/2012 | Thiel et al. | |
| 8,310,683 B2 | 11/2012 | Babayoff et al. | |
| 8,320,621 B2 | 11/2012 | McEldowney | |
| 8,326,020 B2 | 12/2012 | Lee et al. | |
| 8,330,804 B2 | 12/2012 | Lutian et al. | |
| 8,395,342 B2 | 3/2013 | Prisco | |
| 8,400,494 B2 | 3/2013 | Zalevsky et al. | |
| 8,406,859 B2 | 3/2013 | Zuzak et al. | |
| 8,471,897 B2 | 6/2013 | Rodriguez Ramos et al. | |
| 8,517,928 B2 | 8/2013 | Orihara | |
| 8,553,939 B2 | 10/2013 | Craig et al. | |
| 8,558,873 B2 | 10/2013 | McEldowney | |
| 8,593,507 B2 | 11/2013 | Yahav | |
| 8,610,665 B2 | 12/2013 | Craig et al. | |
| 8,617,102 B2 | 12/2013 | Moll et al. | |
| 8,649,024 B2 | 2/2014 | Colonna De Lega | |
| 8,659,765 B2 | 2/2014 | Ando | |
| 8,723,118 B2 | 5/2014 | McEldowney et al. | |
| 8,723,923 B2 | 5/2014 | Bloom et al. | |
| 8,755,053 B2 | 6/2014 | Fright et al. | |
| 8,792,098 B2 | 7/2014 | Dewald et al. | |
| 8,803,952 B2 | 8/2014 | Katz et al. | |
| 8,823,790 B2 | 9/2014 | Dunn et al. | |
| 8,891,087 B2 | 11/2014 | Zuzak et al. | |
| 8,896,594 B2 | 11/2014 | Xiong et al. | |
| 8,974,378 B2 | 3/2015 | Imaizumi et al. | |
| 9,001,190 B2 | 4/2015 | Olivier, III et al. | |
| 9,057,784 B2 | 6/2015 | Hudman | |
| 9,068,824 B2 | 6/2015 | Findeisen et al. | |
| 9,070,194 B2 | 6/2015 | Lee et al. | |
| 9,072,445 B2 | 7/2015 | Berguer et al. | |
| 9,074,868 B2 | 7/2015 | Bendall et al. | |
| 9,089,277 B2 | 7/2015 | Babayoff et al. | |
| 9,119,552 B2 | 9/2015 | Baumann et al. | |
| 9,135,502 B2 | 9/2015 | Haker et al. | |
| 9,142,025 B2 | 9/2015 | Park et al. | |
| 9,147,253 B2 | 9/2015 | Yee et al. | |
| 9,149,281 B2 | 10/2015 | Bonutti | |
| 9,149,348 B2 | 10/2015 | Wu et al. | |
| 9,155,544 B2 | 10/2015 | Bonutti | |
| 9,157,728 B2 | 10/2015 | Ogawa | |
| 9,157,733 B2 | 10/2015 | Dillon et al. | |
| 9,186,053 B2 | 11/2015 | Viola | |
| 9,192,395 B2 | 11/2015 | Bonutti | |
| 9,198,578 B2 | 12/2015 | Zuzak et al. | |
| 9,204,952 B2 | 12/2015 | Lampalzer | |
| 9,220,570 B2 | 12/2015 | Kim et al. | |
| 9,226,645 B2 | 1/2016 | Ntziachristos | |
| 9,226,673 B2 | 1/2016 | Ferguson, Jr. et al. | |
| 9,226,811 B2 | 1/2016 | Abuzaina | |
| 9,247,865 B2 | 2/2016 | Igarashi et al. | |
| 9,254,076 B2 | 2/2016 | McDowall | |
| 9,254,078 B2 | 2/2016 | McDowall | |
| 9,254,103 B2 | 2/2016 | Krishnaswamy et al. | |
| 9,261,356 B2 | 2/2016 | Lampert et al. | |
| 9,261,358 B2 | 2/2016 | Atiya et al. | |
| 9,271,658 B2 | 3/2016 | Ferguson, Jr. et al. | |
| 9,274,047 B2 | 3/2016 | Velten et al. | |
| 9,282,926 B2 | 3/2016 | Schwotzer et al. | |
| 9,294,758 B2 | 3/2016 | Xiong et al. | |
| 9,297,889 B2 | 3/2016 | Hudman et al. | |
| 9,304,603 B2 | 4/2016 | Miller | |
| 9,330,464 B1 | 5/2016 | Ackerman et al. | |
| 9,345,389 B2 | 5/2016 | Nie et al. | |
| 9,345,392 B2 | 5/2016 | Saito | |
| 9,345,397 B2 | 5/2016 | Taylor et al. | |
| 9,351,643 B2 | 5/2016 | Sharonov | |
| 9,364,300 B2 | 6/2016 | Tchouprakov et al. | |
| 9,375,844 B2 | 6/2016 | Itkowitz et al. | |

(56) References Cited

U.S. PATENT DOCUMENTS

| | | | |
|---|---|---|---|
| 9,377,295 B2 | 6/2016 | Fright et al. |
| 9,380,224 B2 | 6/2016 | Keskin et al. |
| 9,389,068 B2 | 7/2016 | Ri |
| 9,402,986 B2 | 8/2016 | Bell et al. |
| 9,404,741 B2 | 8/2016 | Schick |
| 9,432,593 B2 | 8/2016 | Yang et al. |
| 9,439,568 B2 | 9/2016 | Atiya et al. |
| 9,443,310 B2 | 9/2016 | Hudman et al. |
| 9,444,981 B2 | 9/2016 | Bellis et al. |
| 9,451,872 B2 | 9/2016 | Yokota |
| 9,457,168 B2 | 10/2016 | Moll et al. |
| 9,462,253 B2 | 10/2016 | Hudman et al. |
| 9,471,864 B2 | 10/2016 | Zatloukal et al. |
| 9,491,441 B2 | 11/2016 | Sarmast et al. |
| 9,494,418 B2 | 11/2016 | Schmidt |
| 9,506,749 B2 | 11/2016 | Bellis et al. |
| 9,513,113 B2 | 12/2016 | Yang et al. |
| 9,513,768 B2 | 12/2016 | Zhao et al. |
| 9,545,220 B2 | 1/2017 | Sidlesky |
| 9,557,574 B2 | 1/2017 | McEldowney |
| 9,581,802 B2 | 2/2017 | Yokota |
| 9,585,600 B2 | 3/2017 | Sharonov |
| 9,615,901 B2 | 4/2017 | Babayoff et al. |
| 9,622,644 B2 | 4/2017 | Yokota |
| 9,622,662 B2 | 4/2017 | Zuzak et al. |
| 9,638,801 B2 | 5/2017 | Boufounos et al. |
| 9,662,018 B2 | 5/2017 | Stopek |
| 9,674,436 B2 | 6/2017 | Crane et al. |
| 9,675,429 B2 | 6/2017 | Lampert et al. |
| 9,690,984 B2 | 6/2017 | Butler et al. |
| 9,696,427 B2 | 7/2017 | Wilson et al. |
| 9,720,506 B2 | 8/2017 | Kim et al. |
| 9,729,860 B2 | 8/2017 | Cohen et al. |
| 9,737,239 B2 | 8/2017 | Kimmel |
| 9,739,594 B2 | 8/2017 | Koerner et al. |
| 9,746,318 B2 | 8/2017 | Sugano |
| 9,752,867 B2 | 9/2017 | Atiya et al. |
| 9,782,056 B2 | 10/2017 | McDowall |
| 9,788,903 B2 | 10/2017 | Kim et al. |
| 9,799,117 B2 | 10/2017 | Chen et al. |
| 9,817,159 B2 | 11/2017 | Hudman |
| 9,821,456 B2 | 11/2017 | Riedel |
| 9,833,145 B2 | 12/2017 | Jeong et al. |
| 9,841,496 B2 | 12/2017 | Hudman |
| 9,844,427 B2 | 12/2017 | Atiya et al. |
| 9,901,409 B2 | 2/2018 | Yang et al. |
| 9,918,640 B2 | 3/2018 | Ntziachristos et al. |
| 9,922,249 B2 | 3/2018 | Kang et al. |
| 9,939,258 B2 | 4/2018 | Lampert et al. |
| 9,943,271 B2 | 4/2018 | Dirauf et al. |
| 9,943,964 B2 | 4/2018 | Hares |
| 9,947,099 B2 | 4/2018 | Bleyer et al. |
| 9,953,428 B2 | 4/2018 | Gren et al. |
| 9,955,140 B2 | 4/2018 | Rhemann et al. |
| 9,955,861 B2 | 5/2018 | Gao et al. |
| 9,958,585 B2 | 5/2018 | Powell et al. |
| 9,958,758 B2 | 5/2018 | Hudman |
| 9,962,244 B2 | 5/2018 | Esbech et al. |
| 9,970,753 B2 | 5/2018 | Han et al. |
| 10,011,014 B2 | 7/2018 | Divoky et al. |
| 10,018,464 B2 | 7/2018 | Boles et al. |
| 10,024,968 B2 | 7/2018 | Hudman et al. |
| 10,039,439 B2 | 8/2018 | Aoyama |
| 10,045,882 B2 | 8/2018 | Balicki et al. |
| 10,055,856 B2 | 8/2018 | Sabater et al. |
| 10,058,256 B2 | 8/2018 | Chen et al. |
| 10,066,997 B2 | 9/2018 | Korner et al. |
| 10,089,737 B2 | 10/2018 | Krieger et al. |
| 10,244,991 B2 | 4/2019 | Shademan et al. |
| 10,390,718 B2 | 8/2019 | Chen et al. |
| 10,398,519 B2 | 9/2019 | Kim et al. |
| 10,675,040 B2 | 6/2020 | Kim et al. |
| 10,722,173 B2 | 7/2020 | Chen et al. |
| 10,792,492 B2 | 10/2020 | Chen et al. |
| 10,948,350 B2 | 3/2021 | Ferguson, Jr. et al. |
| 11,135,028 B2 | 10/2021 | Kim et al. |
| 11,278,220 B2 | 3/2022 | Tucker et al. |
| 2002/0082612 A1* | 6/2002 | Moll ............ G16H 40/63 606/130 |
| 2003/0083650 A1 | 5/2003 | Wang et al. |
| 2003/0083651 A1 | 5/2003 | Wang et al. |
| 2003/0195623 A1 | 10/2003 | Marchitto et al. |
| 2004/0073257 A1 | 4/2004 | Spitz |
| 2004/0176751 A1 | 9/2004 | Weitzner et al. |
| 2005/0090840 A1 | 4/2005 | Gerbino et al. |
| 2005/0096515 A1 | 5/2005 | Geng |
| 2006/0020272 A1 | 1/2006 | Gildenberg |
| 2006/0258938 A1 | 11/2006 | Hoffman et al. |
| 2007/0115484 A1 | 5/2007 | Huang et al. |
| 2007/0146719 A1 | 6/2007 | Wedel |
| 2007/0165243 A1 | 7/2007 | Kang et al. |
| 2007/0213749 A1 | 9/2007 | Kogasaka et al. |
| 2007/0232855 A1 | 10/2007 | Weitzner et al. |
| 2007/0239178 A1 | 10/2007 | Weitzner et al. |
| 2007/0249911 A1 | 10/2007 | Simon |
| 2007/0250072 A1 | 10/2007 | Weitzner et al. |
| 2007/0250097 A1 | 10/2007 | Weitzner et al. |
| 2007/0280423 A1 | 12/2007 | Schmidt |
| 2007/0293734 A1 | 12/2007 | Coste-Maniere et al. |
| 2008/0013809 A1 | 1/2008 | Zhu et al. |
| 2008/0107305 A1 | 5/2008 | Vanderkooy et al. |
| 2008/0177281 A1 | 7/2008 | Weitzner et al. |
| 2008/0266391 A1 | 10/2008 | Lee et al. |
| 2009/0221874 A1 | 9/2009 | Vinther et al. |
| 2009/0244260 A1 | 10/2009 | Takahashi et al. |
| 2009/0326324 A1 | 12/2009 | Munoz Martinez et al. |
| 2010/0081875 A1 | 4/2010 | Fowler et al. |
| 2010/0113921 A1 | 5/2010 | Fear et al. |
| 2011/0015518 A1 | 1/2011 | Schmidt et al. |
| 2011/0043609 A1 | 2/2011 | Choi et al. |
| 2011/0057930 A1 | 3/2011 | Keller et al. |
| 2011/0080471 A1 | 4/2011 | Song et al. |
| 2011/0123098 A1 | 5/2011 | Ernst et al. |
| 2011/0202068 A1 | 8/2011 | Diolaiti et al. |
| 2012/0075432 A1 | 3/2012 | Bilbrey et al. |
| 2012/0095354 A1 | 4/2012 | Dunn et al. |
| 2012/0130405 A1 | 5/2012 | Cohn et al. |
| 2012/0165681 A1 | 6/2012 | Keller |
| 2012/0206587 A1 | 8/2012 | Oz et al. |
| 2012/0310098 A1 | 12/2012 | Popovic |
| 2013/0023732 A1 | 1/2013 | Kim et al. |
| 2013/0079928 A1 | 3/2013 | Søe-Knudsen et al. |
| 2013/0085595 A1 | 4/2013 | Kiley et al. |
| 2013/0096576 A1 | 4/2013 | Cooper et al. |
| 2013/0253313 A1 | 9/2013 | Kang et al. |
| 2013/0274596 A1 | 10/2013 | Azizian et al. |
| 2013/0296712 A1 | 11/2013 | Durvasula |
| 2013/0304084 A1 | 11/2013 | Beira et al. |
| 2013/0331644 A1 | 12/2013 | Pandya et al. |
| 2014/0031665 A1 | 1/2014 | Pinto et al. |
| 2014/0052005 A1 | 2/2014 | Yokota |
| 2014/0092281 A1 | 4/2014 | Nisenzon et al. |
| 2014/0148816 A1 | 5/2014 | McDonald et al. |
| 2014/0148819 A1 | 5/2014 | Inoue et al. |
| 2014/0194747 A1 | 7/2014 | Kruglick et al. |
| 2014/0243850 A1 | 8/2014 | Sadaka |
| 2014/0257329 A1 | 9/2014 | Jang et al. |
| 2014/0276950 A1* | 9/2014 | Smaby ............ A61B 34/70 606/130 |
| 2014/0277741 A1 | 9/2014 | Kwon et al. |
| 2014/0330288 A1* | 11/2014 | Date ............ A61B 34/37 606/130 |
| 2015/0012016 A1 | 1/2015 | Stone |
| 2015/0164329 A1 | 6/2015 | Schmidt et al. |
| 2015/0238276 A1 | 8/2015 | Atarot et al. |
| 2015/0266183 A1 | 9/2015 | Alifragkis et al. |
| 2015/0377613 A1 | 12/2015 | Small et al. |
| 2016/0128553 A1 | 5/2016 | Geng |
| 2016/0136805 A1 | 5/2016 | Soe-Knudsen et al. |
| 2016/0139039 A1 | 5/2016 | Ikehara et al. |
| 2016/0157942 A1 | 6/2016 | Gombert et al. |
| 2016/0206391 A1 | 7/2016 | Deodhar |
| 2016/0239978 A1 | 8/2016 | Cole et al. |
| 2016/0260206 A1 | 9/2016 | Jung et al. |

(56) References Cited

U.S. PATENT DOCUMENTS

| | | |
|---|---|---|
| 2016/0262615 A1 | 9/2016 | Jung et al. |
| 2016/0278678 A1 | 9/2016 | Valdes et al. |
| 2016/0296225 A1 | 10/2016 | Rohl et al. |
| 2016/0300348 A1 | 10/2016 | Nadeau et al. |
| 2016/0307325 A1 | 10/2016 | Wang et al. |
| 2016/0307326 A1 | 10/2016 | Wang |
| 2016/0309068 A1 | 10/2016 | Nadeau et al. |
| 2016/0335472 A1 | 11/2016 | Lee et al. |
| 2016/0346930 A1 | 12/2016 | Hares |
| 2017/0014030 A1 | 1/2017 | Rentschler et al. |
| 2017/0020393 A1 | 1/2017 | Rentschler et al. |
| 2017/0020615 A1 | 1/2017 | Koenig et al. |
| 2017/0026633 A1 | 1/2017 | Riza |
| 2017/0030710 A1 | 2/2017 | Rentschler et al. |
| 2017/0032531 A1 | 2/2017 | Nagata et al. |
| 2017/0059305 A1 | 3/2017 | Nonn et al. |
| 2017/0079724 A1 | 3/2017 | Yang et al. |
| 2017/0100024 A1 | 4/2017 | Shahmoon et al. |
| 2017/0112368 A1 | 4/2017 | Stern et al. |
| 2017/0112576 A1 | 4/2017 | Coste-Maniere et al. |
| 2017/0143237 A1 | 5/2017 | Yokota |
| 2017/0164836 A1 | 6/2017 | Krishnaswamy et al. |
| 2017/0172382 A1 | 6/2017 | Nir et al. |
| 2017/0172384 A1 | 6/2017 | Yokota |
| 2017/0172801 A1* | 6/2017 | Raksi ............... A61F 9/00804 |
| 2017/0209031 A1 | 7/2017 | Nakamura et al. |
| 2017/0227942 A1 | 8/2017 | Thomson et al. |
| 2017/0228879 A1 | 8/2017 | Sato |
| 2017/0251900 A1 | 9/2017 | Hansen et al. |
| 2017/0280970 A1 | 10/2017 | Sartor et al. |
| 2017/0328704 A1 | 11/2017 | Atiya et al. |
| 2017/0333030 A1 | 11/2017 | Bourland, III et al. |
| 2017/0347043 A1 | 11/2017 | Rephaeli et al. |
| 2017/0366773 A1 | 12/2017 | Kiraly et al. |
| 2018/0003943 A1 | 1/2018 | Chan |
| 2018/0008371 A1 | 1/2018 | Manus |
| 2018/0042466 A1 | 2/2018 | Kang et al. |
| 2018/0047165 A1 | 2/2018 | Sato |
| 2018/0104009 A1 | 4/2018 | Abhari et al. |
| 2018/0125586 A1 | 5/2018 | Sela et al. |
| 2018/0165823 A1 | 6/2018 | Ludwig |
| 2018/0174318 A1 | 6/2018 | Wang et al. |
| 2018/0214241 A1 | 8/2018 | Furuta et al. |
| 2018/0235715 A1 | 8/2018 | Amiot et al. |
| 2018/0243043 A1 | 8/2018 | Michihata et al. |
| 2018/0338806 A1 | 11/2018 | Grubbs |
| 2018/0345492 A1 | 12/2018 | Watanabe et al. |
| 2019/0209241 A1* | 7/2019 | Begg ............... A61B 17/3423 |
| 2020/0305721 A1 | 10/2020 | Chen et al. |
| 2021/0030277 A1 | 2/2021 | Ferguson, Jr. et al. |
| 2021/0077195 A1* | 3/2021 | Saeidi ............... A61B 34/32 |
| 2021/0282654 A1 | 9/2021 | Cha et al. |
| 2021/0354285 A1 | 11/2021 | Buharin et al. |
| 2022/0015844 A1 | 1/2022 | Dehghani |
| 2022/0020160 A1 | 1/2022 | Buharin |
| 2022/0175471 A1 | 6/2022 | Pickett et al. |

FOREIGN PATENT DOCUMENTS

| | | |
|---|---|---|
| WO | WO-2010096453 A1 | 8/2010 |
| WO | WO-2012096878 A2 | 7/2012 |
| WO | WO-2014152753 A1 | 9/2014 |
| WO | WO-2015070010 A1 | 5/2015 |
| WO | WO-2016061052 A1 | 4/2016 |
| WO | WO-2016153741 A1 | 9/2016 |
| WO | WO-2017075602 A1 | 5/2017 |
| WO | WO-2018067515 A1 | 4/2018 |
| WO | WO-2019045971 A1 | 3/2019 |
| WO | WO-2020006454 A1 | 1/2020 |
| WO | WO-2020118244 A1 | 6/2020 |
| WO | WO-2020140042 | 7/2020 |
| WO | WO-2020140048 A1 | 7/2020 |
| WO | WO-2020140056 | 7/2020 |
| WO | WO-2020214821 | 11/2020 |
| WO | WO-2022029308 A1 | 2/2022 |
| WO | WO-2022058499 A1 | 3/2022 |

OTHER PUBLICATIONS

EP19901561.1 Extended European Search Report dated Jan. 4, 2023.

EP19902562.8 Extended Search Report dated Aug. 22, 2022.

Holstein-Rathlou et al. Nephron blood flow dynamics measured by laser speckle contrast imaging. Am J Physiol Renal Physiol 300: F319-F329, 2011.

PCT/US19/068756 Search Report & Written Opinion dated Apr. 1, 2020.

PCT/US19/068765 Search Report & Written Opinion dated Apr. 1, 2020.

PCT/US19/65056 International Search Report and Written Opinion dated Nov. 6, 2020.

PCT/US20/28536 Search Report & Written Opinion dated Jul. 21, 2020.

Richards et al. Intraoperative laser speckle contrast imaging with retrospective motion correction for quantitative assessment of cerebral blood flow. Neurophotonics 1(1), 015006 (Jul.-Sep. 2014).

Richards et al. Low-cost laser speckle contrast imaging of blood flow using a webcam. 2013 Optical Society of America.

U.S. Appl. No. 17/338,030 Office Action dated Oct. 4, 2023.

PCT/US19/068778 Search Report & Written Opinion dated Apr. 1, 2020.

\* cited by examiner

SYSTEMS AND METHODS TO OPTIMIZE REACHABILITY, WORKSPACE, AND DEXTERITY IN MINIMALLY INVASIVE SURGERY

CROSS-REFERENCE TO RELATED APPLICATION

This application is a continuation application of International Application No. PCT/US2019/068778, filed on Dec. 27, 2019, which application claims the benefit of U.S. Provisional Patent Application No. 62/785,957, filed on Dec. 28, 2018, which applications are incorporated herein by reference in their entirety for all purposes.

BACKGROUND

Embodiments of the present disclosure generally relate to optimization of reachability, workspace, and dexterity of a minimally invasive surgical robot. In particular, the present disclosure describes a method of determining an error-minimizing incision placement to optimize the reachability, workspace, and dexterity of the surgical robot.

BRIEF SUMMARY

According to embodiments of the present disclosure, systems for, methods for, and computer program products for determining an error-minimizing workspace for a surgical robot are provided. In various embodiments, the system includes a first robotic arm having a proximal end and a distal end. The proximal end is fixed to a base. The system further includes a surgical instrument disposed at the distal end of the robotic arm and the surgical instrument has a proximal end and a distal end. The system further includes a tool coupled to the distal end of the surgical instrument and a computing node including a computer readable storage medium having program instructions embodied therewith. The program instructions are executable by a processor of the computing node to cause the processor to perform a method where an error-minimizing incision site is determined in a patient. A tool orientation error for the tool is determined based on one or more locations of anatomical structures and the error-minimizing incision site. The surgical robot is adjusted based on the tool orientation error thereby minimizing the tool orientation error.

In various embodiments, a surgical trajectory to the one or more locations of anatomical structures may be determined. In various embodiments, the surgical trajectory is discretized with a plurality of points defined along the surgical trajectory. In various embodiments, the tool orientation error is determined for each of the plurality of points along the surgical trajectory. In various embodiments, the tool orientation error is determined by: $error = \alpha^2 + \beta^2 + \gamma^2$ where $\alpha$ is an angle between a desired x-component and actual x-component of the tool, $\beta$ is an angle between a desired y-component and actual y-component of the tool, and $\gamma$ is an angle between a desired z-component and actual z-component of the tool. In various embodiments, determining an error-minimizing incision site in a patient includes discretizing a surface of an anatomical model of the patient thereby generating a plurality of candidate incision sites on the surface. In various embodiments, determining the error-minimizing incision site in a patient includes determining tool orientation error for each of the plurality of candidate incision sites. In various embodiments, one of the plurality of candidate incision sites having a smallest error metric is selected. In various embodiments, an error-minimizing position of a base of the surgical robot is determined and the error-minimizing position is based on the selected incision site. In various embodiments, determining the error-minimizing position of the base includes discretizing a space exterior to the patient into a plurality of candidate base locations. In various embodiments, a second tool orientation error based on the discretized surgical trajectory is determined for each of the plurality of candidate base locations. In various embodiments, the second tool orientation error is determined by: $error = \alpha^2 + \beta^2 + \gamma^2$ where $\alpha$ is an angle between a desired x-component and actual x-component of the tool, $\beta$ is an angle between a desired y-component and actual y-component of the tool, and $\gamma$ is an angle between a desired z-component and actual z-component of the tool.

In various embodiments, a method is provided for determining an error-minimizing workspace for a surgical robot having a proximal end and a distal end and a surgical instrument at the distal end having a tool, where an error-minimizing incision site in a patient is determined. A tool orientation error for the tool is determined based on one or more locations of anatomical structures and the error-minimizing incision site. The surgical robot is adjusted based on the tool orientation error thereby minimizing the tool orientation error.

In various embodiments, a surgical trajectory to the one or more locations of anatomical structures may be determined. In various embodiments, the surgical trajectory is discretized with a plurality of points defined along the surgical trajectory. In various embodiments, the tool orientation error is determined for each of the plurality of points along the surgical trajectory. In various embodiments, the tool orientation error is determined by: $error = \alpha^2 + \beta^2 + \gamma^2$ where $\alpha$ is an angle between a desired x-component and actual x-component of the tool, $\beta$ is an angle between a desired y-component and actual y-component of the tool, and $\gamma$ is an angle between a desired z-component and actual z-component of the tool. In various embodiments, determining an error-minimizing incision site in a patient includes discretizing a surface of an anatomical model of the patient thereby generating a plurality of candidate incision sites on the surface. In various embodiments, determining the error-minimizing incision site in a patient includes determining tool orientation error for each of the plurality of candidate incision sites. In various embodiments, one of the plurality of candidate incision sites having a smallest error metric is selected. In various embodiments, an error-minimizing position of a base of the surgical robot is determined and the error-minimizing position is based on the selected incision site. In various embodiments, determining the error-minimizing position of the base includes discretizing a space exterior to the patient into a plurality of candidate base locations. In various embodiments, a second tool orientation error based on the discretized surgical trajectory is determined for each of the plurality of candidate base locations. In various embodiments, the second tool orientation error is determined by: $error = \alpha^2 + \beta^2 + \gamma^2$ where $\alpha$ is an angle between a desired x-component and actual x-component of the tool, $\beta$ is an angle between a desired y-component and actual y-component of the tool, and $\gamma$ is an angle between a desired z-component and actual z-component of the tool.

In various embodiments, computer program products for determining an error-minimizing workspace for a surgical robot having a proximal end and a distal end and a surgical instrument at the distal end having a tool are provided. The computer program product includes a computer readable storage medium having program instructions embodied therewith. The program instructions are executable by a processor of the computing node to cause the processor to perform a method where an error-minimizing incision site is determined in a patient. A tool orientation error for the tool is determined based on one or more locations of anatomical structures and the error-minimizing incision site. The surgical robot is adjusted based on the tool orientation error thereby minimizing the tool orientation error.

In various embodiments, a surgical trajectory to the one or more locations of anatomical structures may be determined. In various embodiments, the surgical trajectory is discretized with a plurality of points defined along the surgical trajectory. In various embodiments, the tool orientation error is determined for each of the plurality of points along the surgical trajectory. In various embodiments, the tool orientation error is determined by: error=$\alpha^2+\beta^2+\gamma^2$ where $\alpha$ is an angle between a desired x-component and actual x-component of the tool, $\beta$ is an angle between a desired y-component and actual y-component of the tool, and $\gamma$ is an angle between a desired z-component and actual z-component of the tool. In various embodiments, determining an error-minimizing incision site in a patient includes discretizing a surface of an anatomical model of the patient thereby generating a plurality of candidate incision sites on the surface. In various embodiments, determining the error-minimizing incision site in a patient includes determining tool orientation error for each of the plurality of candidate incision sites. In various embodiments, one of the plurality of candidate incision sites having a smallest error metric is selected. In various embodiments, an error-minimizing position of a base of the surgical robot is determined and the error-minimizing position is based on the selected incision site. In various embodiments, determining the error-minimizing position of the base includes discretizing a space exterior to the patient into a plurality of candidate base locations. In various embodiments, a second tool orientation error based on the discretized surgical trajectory is determined for each of the plurality of candidate base locations. In various embodiments, the second tool orientation error is determined by: error=$\alpha^2+\beta^2+\gamma^2$ where $\alpha$ is an angle between a desired x-component and actual x-component of the tool, $\beta$ is an angle between a desired y-component and actual y-component of the tool, and $\gamma$ is an angle between a desired z-component and actual z-component of the tool.

According to embodiments of the present disclosure, systems for, methods for, and computer program products for determining error in tool orientation at a distal end of a surgical instrument of a surgical robot are provided. In various embodiments, a system includes a first robotic arm having a proximal end and a distal end. The proximal end is fixed to a base. A surgical instrument is disposed at the distal end of the robotic arm and the surgical instrument has a proximal end and a distal end. A tool is coupled to the distal end of the surgical instrument. The system further includes a computing node including computer readable storage medium having program instructions embodied therewith. The program instructions are executable by a processor of the computing node to cause the processor to perform a method where a first orientation of the end effector is determined. The first orientation includes a first x-component, a first y-component, and a first z-component. A desired orientation of the end effector is determined. The desired orientation includes a second x-component, a second y-component, and a second z-component. A first angle between the first x-component and the second x-component is determined, a second angle between the first y-component and the second y-component is determined, and a third angle between the first z-component and the second z-component is determined An error metric based on the first angle, the second angle, and the third angle is determined.

In various embodiments, the error metric is determined by: error=$\alpha^2+\beta^2+\gamma^2$ where $\alpha$ is the first angle, $\beta$ is the second angle, and $\gamma$ is the third angle. In various embodiments, an anatomical model of a patient is determined. In various embodiments, a first incision site on the anatomical model is selected and the error metric corresponds to the first incision site. In various embodiments, the anatomical model includes an anatomical atlas. In various embodiments, the anatomical model includes a three-dimensional reconstruction of patient anatomy based on imaging of the patient. In various embodiments, determining the error metric includes maintaining a fixed three-dimensional position at a proximal location along the surgical instrument. In various embodiments, the proximal location corresponds to the incision site on the anatomical model. In various embodiments, the anatomical model comprises a target anatomical structure. In various embodiments, one or more additional error metrics are determined such that each of the additional error metrics corresponds to a different location of a plurality of locations within the anatomical model. In various embodiments, the different locations correspond to a 2D Cartesian grid. In various embodiments, a graph of error metrics for each of the plurality of locations within the anatomical model is displayed. In various embodiments, the method further includes selecting a one or more additional incision sites on the anatomical model and, for each additional incision site, determining a map of error metrics for each of a plurality of locations within the anatomical model. In various embodiments, one of the incision sites having the smallest error metric is selected.

In various embodiments, a method for determining error in the orientation of an end effector is provided where a first orientation of the end effector is determined. The first orientation includes a first x-component, a first y-component, and a first z-component. A desired orientation of the end effector is determined. The desired orientation includes a second x-component, a second y-component, and a second z-component. A first angle between the first x-component and the second x-component is determined, a second angle between the first y-component and the second y-component is determined, and a third angle between the first z-component and the second z-component is determined An error metric based on the first angle, the second angle, and the third angle is determined.

In various embodiments, the error metric is determined by: error=$\alpha^2+\beta^2+\gamma^2$ where $\alpha$ is the first angle, $\beta$ is the second angle, and $\gamma$ is the third angle. In various embodiments, an anatomical model of a patient is determined. In various embodiments, a first incision site on the anatomical model is selected and the error metric corresponds to the first incision site. In various embodiments, the anatomical model includes an anatomical atlas. In various embodiments, the anatomical model includes a three-dimensional reconstruction of patient anatomy based on imaging of the patient. In various embodiments, determining the error metric includes maintaining a fixed three-dimensional position at a proximal location along the surgical instrument. In various embodiments, the proximal location corresponds to the incision site on the anatomical model. In various embodiments, the anatomical model comprises a target anatomical structure. In various embodiments, one or more additional error metrics are determined such that each of the additional error metrics corresponds to a different location of a plurality of locations within the anatomical model. In various embodiments, the different locations correspond to a 2D Cartesian grid. In various embodiments, a graph of error metrics for each of the plurality of locations within the anatomical model is displayed. In various embodiments, the method further includes selecting a one or more additional incision sites on the anatomical model and, for each additional incision site, determining a map of error metrics for each of a plurality of locations within the anatomical model. In various embodiments, one of the incision sites having the smallest error metric is selected.

In various embodiments, a computer program product for determining error in the orientation of an end effector is provided in the form of a computer readable storage medium having program instructions embodied therewith. The program instructions are executable by a processor to cause the processor to perform a method where α first orientation of the end effector is determined. The first orientation includes a first x-component, a first y-component, and a first z-component. A desired orientation of the end effector is determined. The desired orientation includes a second x-component, a second y-component, and a second z-component. A first angle between the first x-component and the second x-component is determined, a second angle between the first y-component and the second y-component is determined, and a third angle between the first z-component and the second z-component is determined An error metric based on the first angle, the second angle, and the third angle is determined.

In various embodiments, the error metric is determined by: error=$\alpha^2+\beta^2+\gamma^2$ where $\alpha$ is the first angle, $\beta$ is the second angle, and $\gamma$ is the third angle. In various embodiments, an anatomical model of a patient is determined. In various embodiments, a first incision site on the anatomical model is selected and the error metric corresponds to the first incision site. In various embodiments, the anatomical model includes an anatomical atlas. In various embodiments, the anatomical model includes a three-dimensional reconstruction of patient anatomy based on imaging of the patient. In various embodiments, determining the error metric includes maintaining a fixed three-dimensional position at a proximal location along the surgical instrument. In various embodiments, the proximal location corresponds to the incision site on the anatomical model. In various embodiments, the anatomical model comprises a target anatomical structure. In various embodiments, one or more additional error metrics are determined such that each of the additional error metrics corresponds to a different location of a plurality of locations within the anatomical model. In various embodiments, the different locations correspond to a 2D Cartesian grid. In various embodiments, a graph of error metrics for each of the plurality of locations within the anatomical model is displayed. In various embodiments, the method further includes selecting a one or more additional incision sites on the anatomical model and, for each additional incision site, determining a map of error metrics for each of a plurality of locations within the anatomical model. In various embodiments, one of the incision sites having the smallest error metric is selected.

DETAILED DESCRIPTION

Many surgical maneuvers (e.g., suturing, cutting, and/or folding) require highly dexterous and highly accurate motion of surgical tools to achieve a satisfactory surgical outcome. In fully automated robotic surgical procedures, surgical robots generally include a surgical instrument attached thereto having a tool that is inserted through a trocar placed in a small, keyhole incision in the abdomen of a patient. A keyhole incision, as used herein, may refer to a minimally invasive incision that is about 0.25 inch to 1 inch in size. The tool may include any suitable medical tool, such as, for example, a camera, a cutting tool, a gripping tool, a crimping tool, an electrocautery tool, or any other suitable tool as is known in the art. When the surgical instrument is inserted through the trocar (and into a body cavity, e.g., abdomen, of the patient), the range of motion and/or possible orientations of the tool may be limited based on the position of the trocar in the patient. If the trocar position is not optimized based on the range of motion and/or possible orientations, the tool may not be capable of reaching certain regions of or objects (e.g., a major artery) within a workspace (e.g., a body cavity) and, thus, may not be able to perform the surgical task (e.g., cutting, gripping, etc.) for which it is intended. For example, if the base of a robotic arm is placed too far away from the patient, an anatomical object (e.g., a kidney) which is a target object of a surgical procedure may be out of the working range of the tool, thus complicating the surgical process.

Accordingly, a need exists for a system and method to determine an error-minimizing incision placement to thereby enable accurate surgical maneuvers and improve robotic-assisted surgery.

Figure 1:
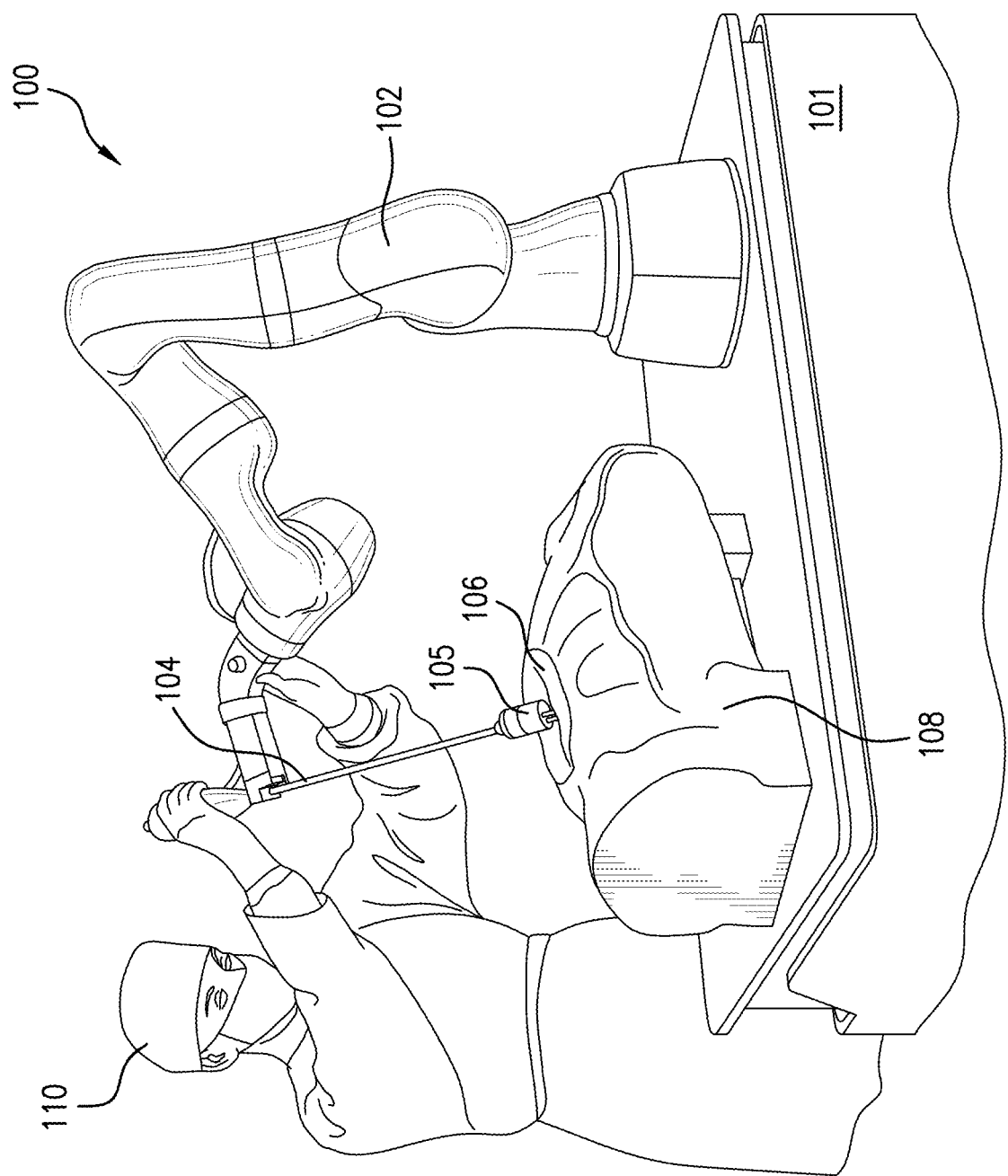
FIG. 1 illustrates a robotic arm system for performing laparoscopic surgery according to an embodiment of the present disclosure.

FIG. 1 illustrates a robotic arm system 100 for performing laparoscopic surgery according to an embodiment of the present disclosure. The robotic arm system 100 includes a robotic arm 102 affixed to a base 101 at a proximal end. The robotic arm 102 further includes a surgical instrument 104 at the distal end and the surgical instrument 104 includes a tool (not shown), such as, for example, a grasper, electrocautery tool, a cutting tool, etc. A trocar 105 is inserted into an incision 106 in the abdomen 108 to thereby provide access to a body cavity (e.g., abdominal cavity) in which a surgical procedure will take place. In various embodiments, a surgeon 110 overseeing the robotic surgery may insert the surgical instrument 104 (and the tool) through the trocar 105 and into the body cavity.

Figure 2A:
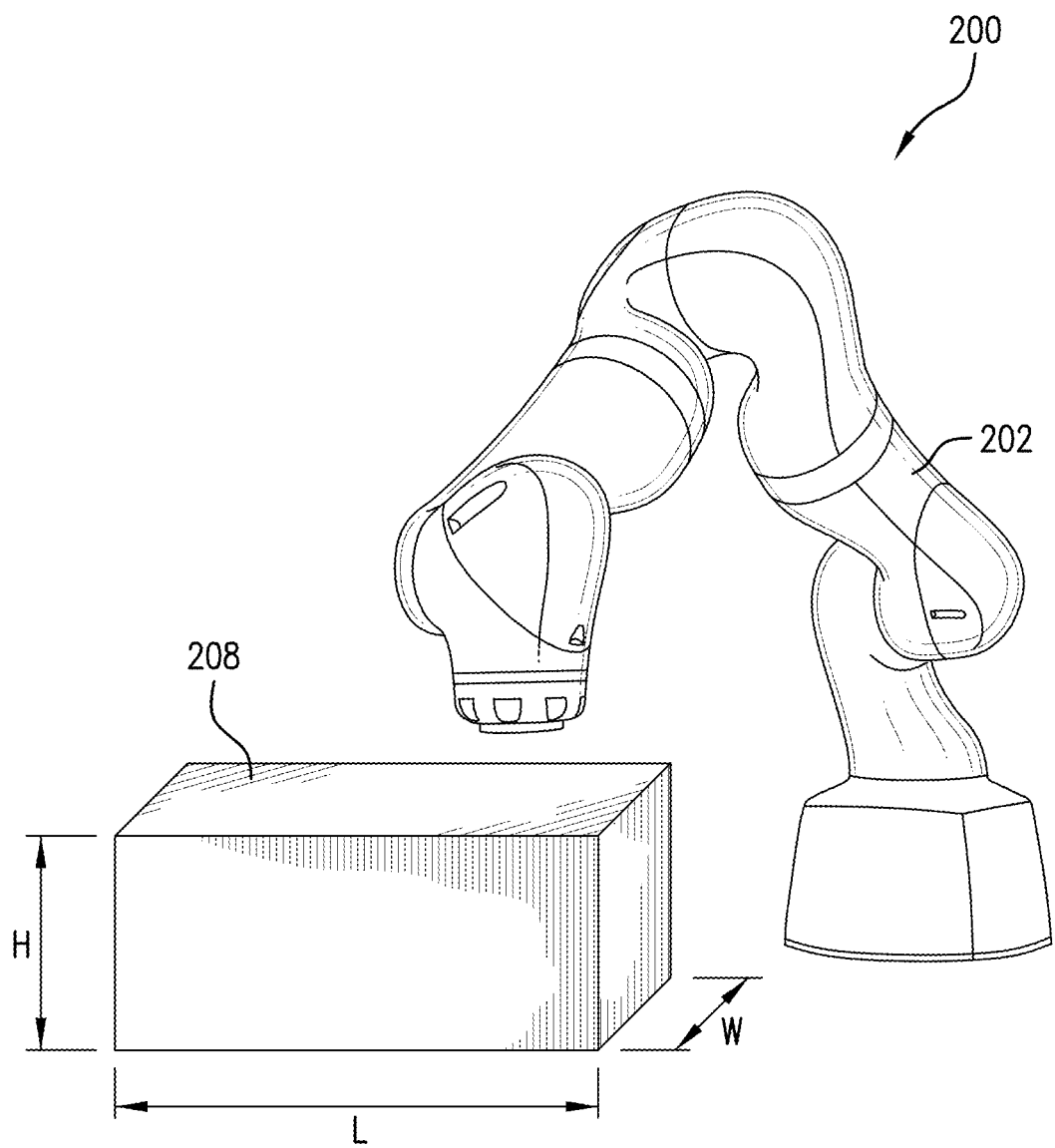
FIGS. 2A-2B illustrate a robotic arm system for performing laparoscopic surgery according to an embodiment of the present disclosure.
Figure 2B:
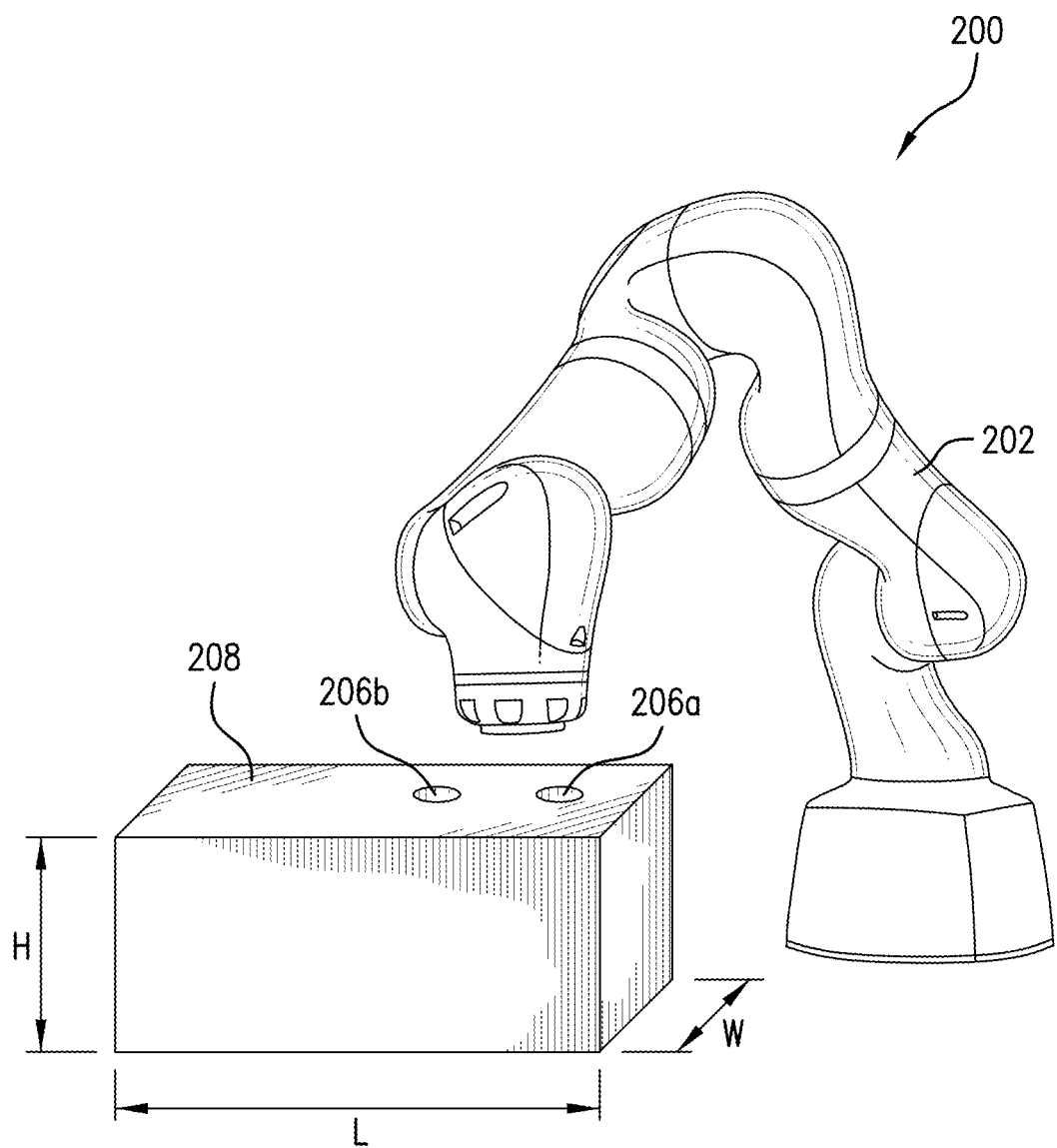

FIGS. 2A-2B illustrate a robotic arm system 200 for performing laparoscopic surgery according to an embodiment of the present disclosure. Similar to the robotic arm system of FIG. 1, the robotic arm system 200 includes a robotic arm 202 positioned over an abdomen 208 (modeled as a rectangular box having dimensions of 40 cm×40 cm×20 cm). In various embodiments, the dimensions of the abdomen 208 may vary based on the particular patient. FIG. 2B shows an abdomen 208 including a first incision 206a corresponding to a first case and a second keyhole incision 206b corresponding to a second case. The tool at the end of the surgical instrument may have a different orientation error depending on the location of the incision for a given surgical process. The variability of end effector orientation error will be discussed in more detail with respect to FIGS. 6A, 6B and 7.

Figure 2C:
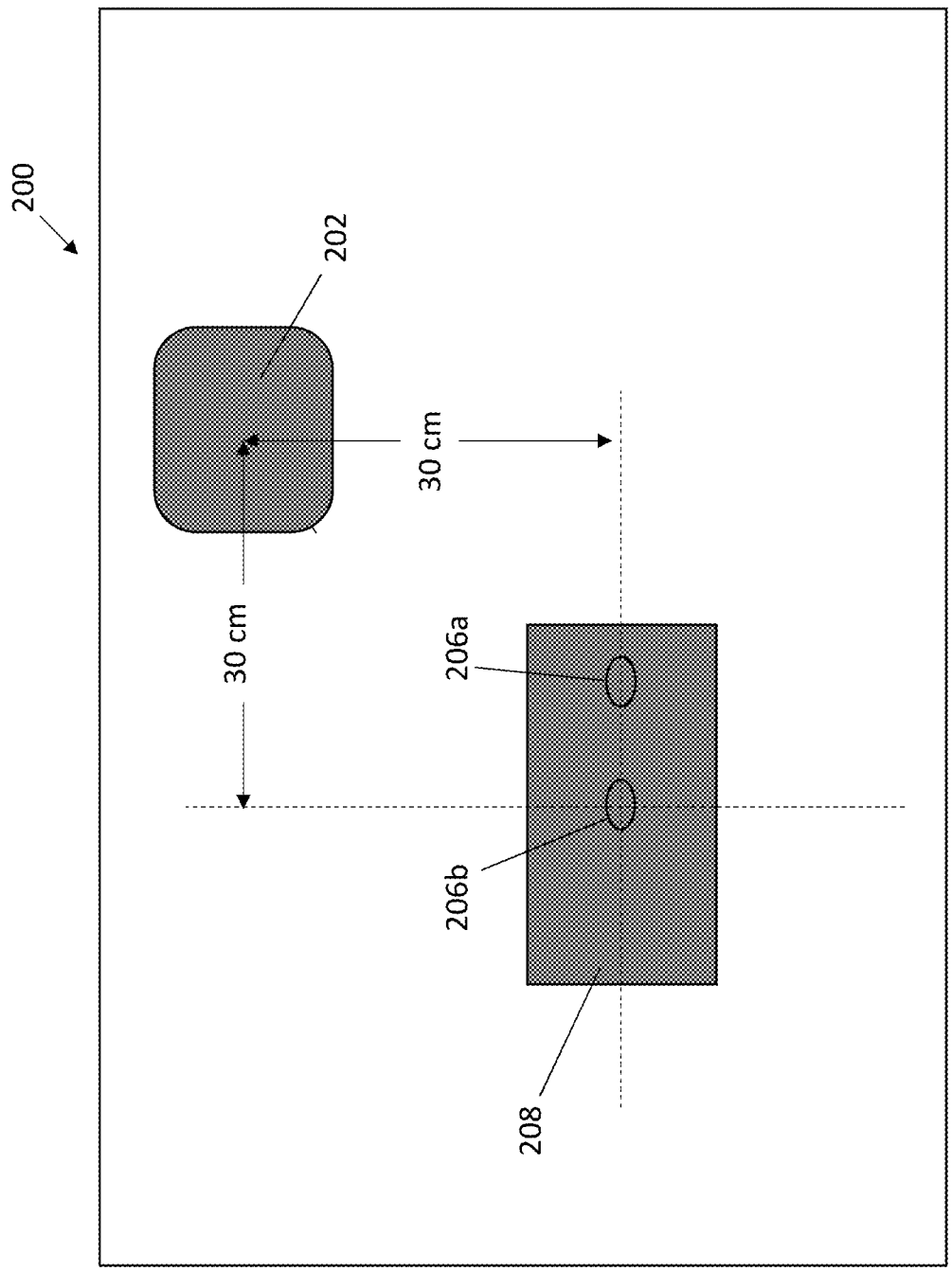
FIG. 2C illustrates a top view of a robotic arm system for performing laparoscopic surgery according to an embodiment of the present disclosure.

FIG. 2C illustrates a top view of a robotic arm system 200 for performing laparoscopic surgery according to an embodiment of the present disclosure. As shown in FIG. 2C, the second keyhole incision 206b in the abdomen 208 (approximately in the center of the abdomen) is positioned approximately 30 cm from the base in either direction. In various embodiments, an optimization algorithm may be applied to each potential incision 206a, 206b to determine the maximum error in the tool based on a particular surgical procedure.

Figure 3A:
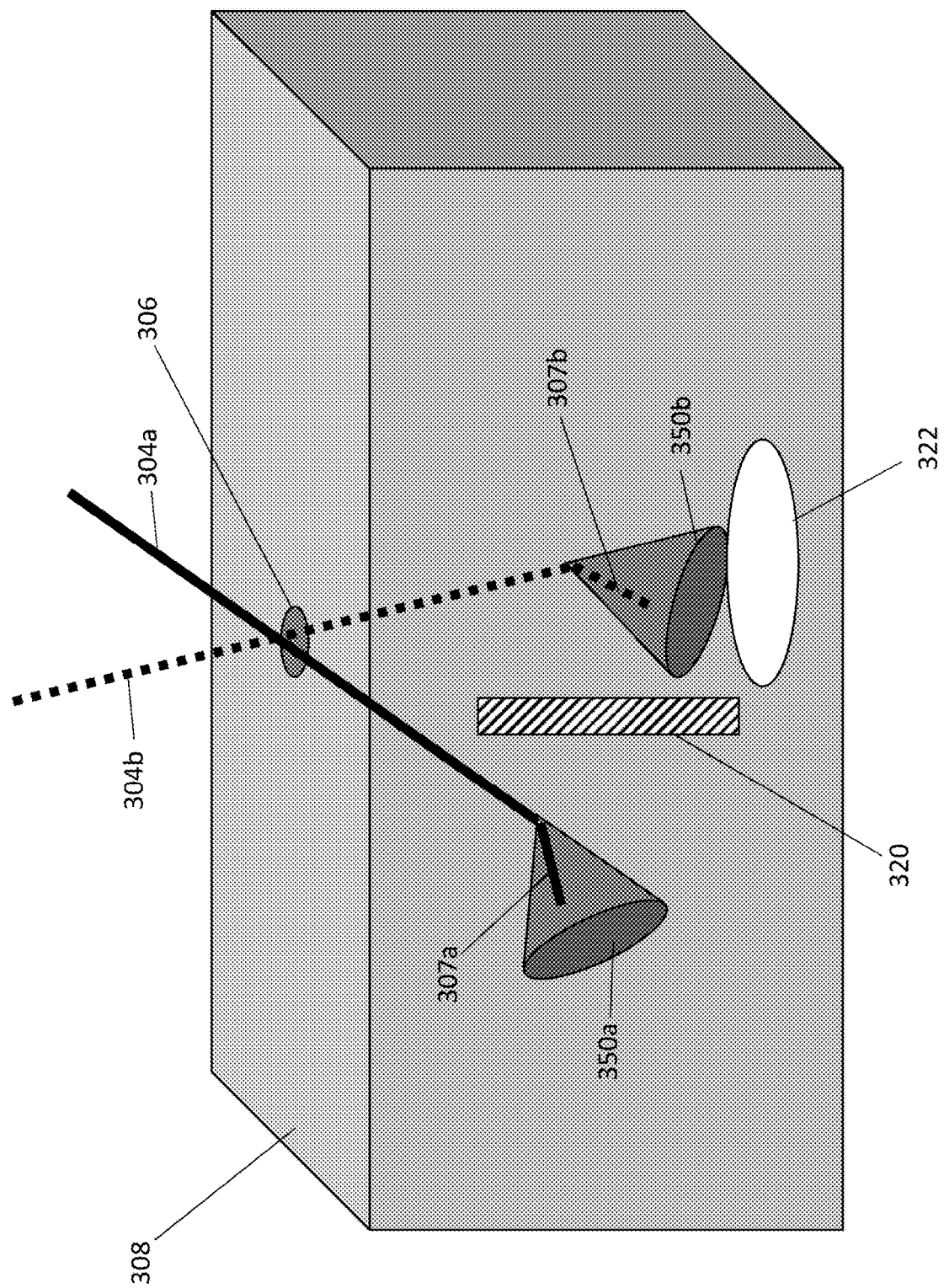
FIG. 3A illustrates two orientations of a surgical instrument and tool within an abdomen according to an embodiment of the present disclosure.

FIG. 3A illustrates two orientations of a surgical instrument 304a, 304b and tool 307a, 307b within an abdomen 308 according to an embodiment of the present disclosure. As shown in FIG. 3A, a surgical instrument 304a and a tool 307a are placed in a first orientation within the incision 306 in the abdomen 308. Due to one or more constraints created by the incision 306 and/or sensitive tissues (e.g., nerves and/or blood vessels), the tool 307a may not be capable of a desired orientation, such as the orientation shown by surgical instrument 304b with the tool 307b having a different orientation than the orientation of the tool 307a. In various embodiments, cone 350a represents all possible orientations of the tool 307a when surgical instrument 304a is in that particular location. In various embodiments, cone 350b represents all possible orientations of the tool 307b when surgical instrument 304b is in that particular location. As shown in FIG. 3A, cone 350b does not collide with object 320 and can access anatomical structure 322.

In various embodiments, the surgical instrument (and tool) may have a limited workspace within a particular body cavity. In various embodiments, one or more objects 320 (e.g., a bone or blood vessel) may prevent the surgical instrument from being capable of adopting a particular desired orientation to access an anatomical structure 322 (e.g., a kidney). In the first orientation, the tool 307a, may not be capable of performing a surgical maneuver on the anatomical structure 322 in certain portions of the abdomen 308, whereas, in the desired orientation, the surgical instrument 304b is capable of performing the surgical maneuver on the anatomical structure 322.

In various embodiments, the surgical instrument (and tool) may have a limited workspace within a particular body cavity based on placement of the base of the robotic arm. In various embodiments, if the base of the robotic arm is incorrectly positioned (e.g., placed too far away from the patient), the surgical instrument may not be capable of adopting a particular, desired orientation (such as the orientation shown by tool 307b of surgical instrument 304b) to access an anatomical structure 322 (e.g., a kidney).

Figure 3B:
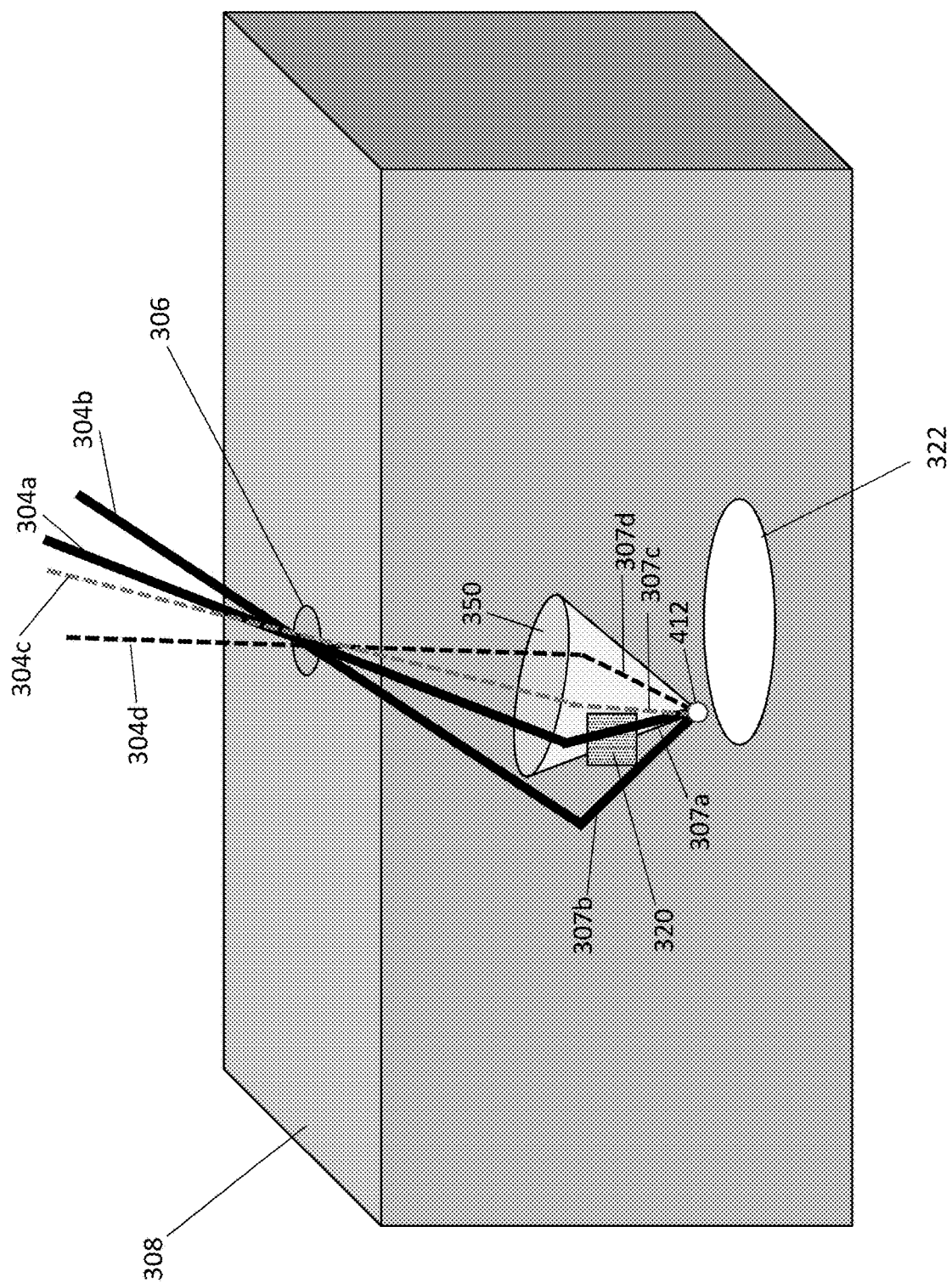
FIG. 3B illustrates various orientations of a surgical instrument and tool within an abdomen according to an embodiment of the present disclosure.

FIG. 3B illustrates various orientations of a surgical instrument 304a, 304b, 304c, 304d and tool 307a, 307b, 307c, 307d within an abdomen 308 according to an embodiment of the present disclosure. In various embodiments, in a first orientation of the surgical instrument 304a, the desired orientation for the tool is not achievable due to the presence of an object 320 (e.g., a nerve and/or vascular structure) blocking the tool. In various embodiments, in a second orientation of the surgical instrument 304b, the desired orientation for the tool is not achievable due to the incision site 306 and/or trocar as only orientations that fall inside the cone 350 are achievable. In various embodiments, tools 307b and 307c may have the least tool orientation error with respect to the desired tool orientation 307a. In this example, 307b is not achievable due to the incision site 306 and, thus, tool 307c orientation would be selected.

In various embodiments, the location if the incision (and subsequent trocar placement) imposes a kinematics constraint on a surgical robot. In various embodiments, one constraint is that the instrument should not move laterally at the incision site (e.g., to avoid damaging the incision). In various embodiments, the maneuverability at the tool may be significantly reduced when a procedure is performed laparoscopically (because of this constraint at the incision/trocar). In various embodiments, if the instrument does not have an articulated distal tool, proper placement of the incision site is important to preserve maneuverability of the instrument given a surgical target (e.g., an organ). In various embodiments, even with a dexterous tool (e.g., a grasper) having one or more articulated joints, the tool may encounter issues when attempting to reach a target from a certain angle because, for example, the incision site restricts the motion of the instrument and/or tool.

Figure 4A:
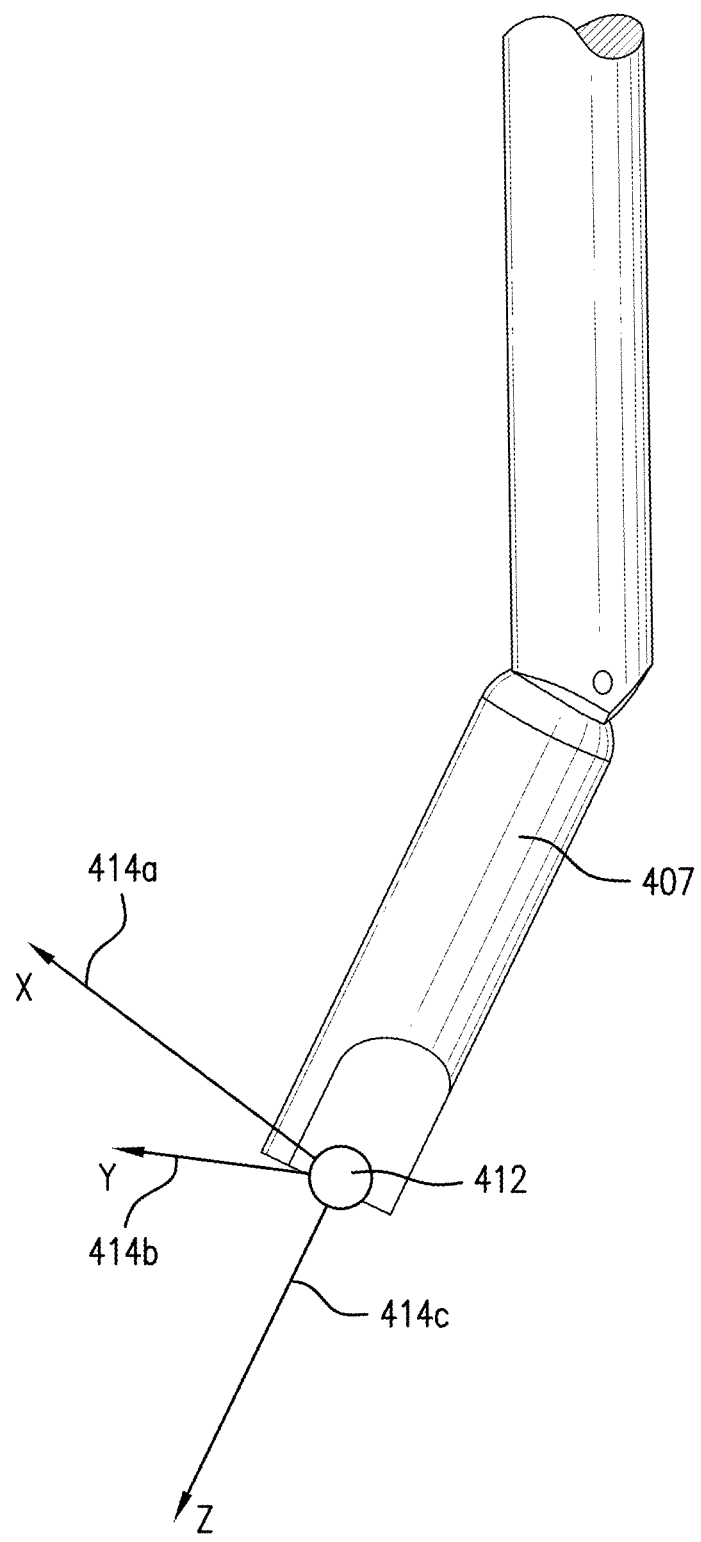
FIGS. 4A-4B illustrate a tool orientation according to an embodiment of the present disclosure.
Figure 4B:
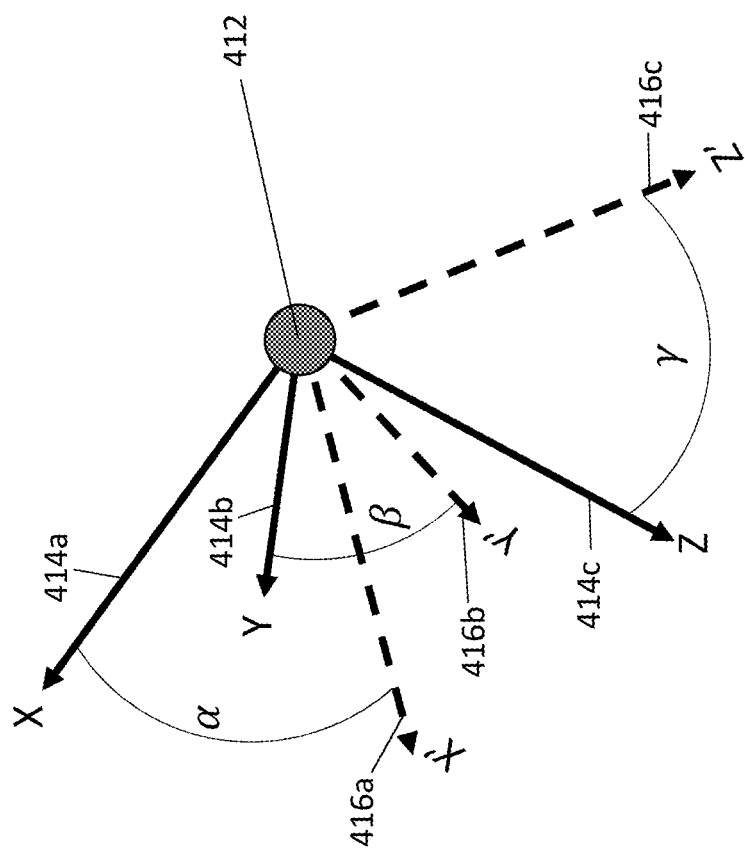

FIGS. 4A-4B illustrate a tool 407 orientation according to an embodiment of the present disclosure. As shown in FIG. 4A, the tool 407 has an orientation based on a distal most point 412. The orientation of the tool 407 includes three vectors: an x-component 414a, a y-component 414b, and a z-component 414c that together define the orientation of the tool 407 in 3D space.

FIG. 4B illustrates the distal point 412 without the tool 407 illustrated in FIG. 4A. As shown in FIG. 4B, the tool 407 includes an actual orientation including the x-component 414a, the y-component 414b, and the z-component 414c. In this case, the actual orientation is different than the desired orientation, which is represented by a x'-component 416a, a y'-component 416b, and a z'-component 416c that together define the desired orientation of the tool 407.

In various embodiments, angles may be measured between the particular axes and their desired configurations. For example, an angle $\alpha$ is measured between the x-component 414a and the x'-component 416a, an angle $\beta$ is measured between the y-component 414b and the y'-component 416b, and an angle $\gamma$ is measured between the z-component 414c and the z'-component 416c. An error metric may be determined using the equation below:

$$\alpha^2 + \beta^2 + \gamma^2 = \text{error} \tag{Eqn. 1}$$

In various embodiments, a surgical target may be identified. In various embodiments, the surgical target may be a tissue, organ, structure, and/or any other suitable target of a surgical procedure.

In various embodiments, a surgical task (e.g., suturing a tissue) may be specified. In various embodiments, the surgical task may be specified with respect to a trajectory of the distal-most end of the tool. In various embodiments, the trajectory may include one or more lines. In various embodiments, the trajectory may include one or more curves. In various embodiments, the trajectory may include a spline.

In various embodiments, the trajectory may be discretized into a finite set of discrete points. In various embodiments, the discretized trajectory may include a set of discrete points having a pre-determined distance between each point. In various embodiments, the pre-determined distance between each point may be different. For example, points along a straight line may have a larger distance between each point while points on a curve may have a smaller distance between each point. In various embodiments, the trajectory may be discretized using any suitable known discretization algorithm.

Figure 6A:
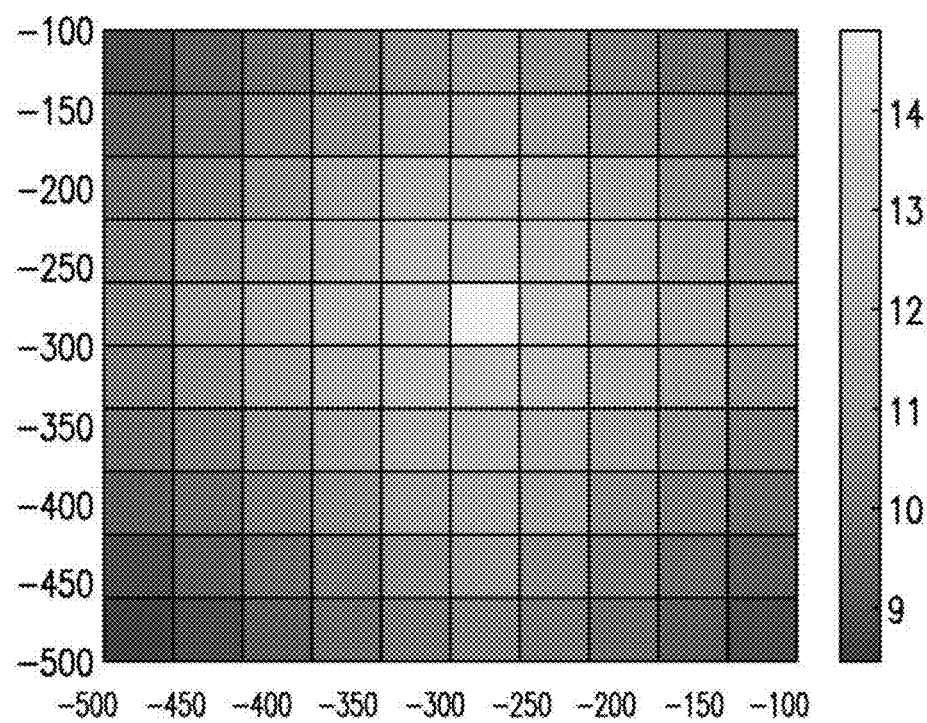
FIGS. 6A-6B illustrate graphical representations of tool orientation error according to an embodiment of the present disclosure.
Figure 6B:
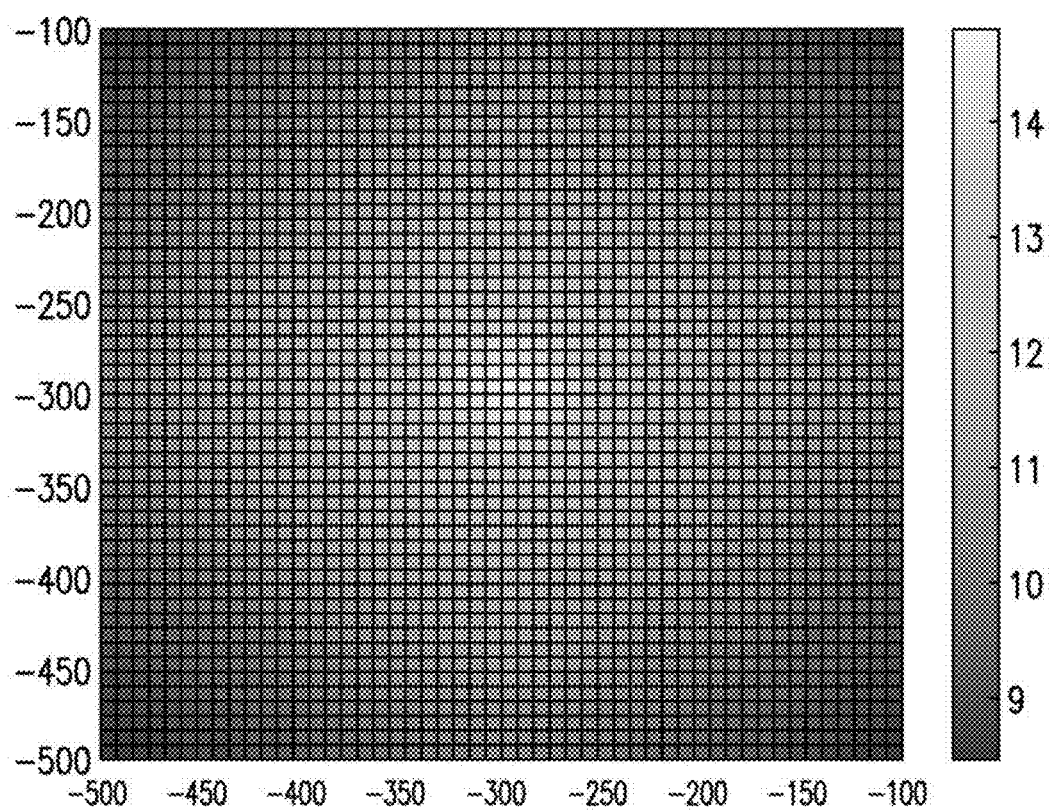
Figure 7:
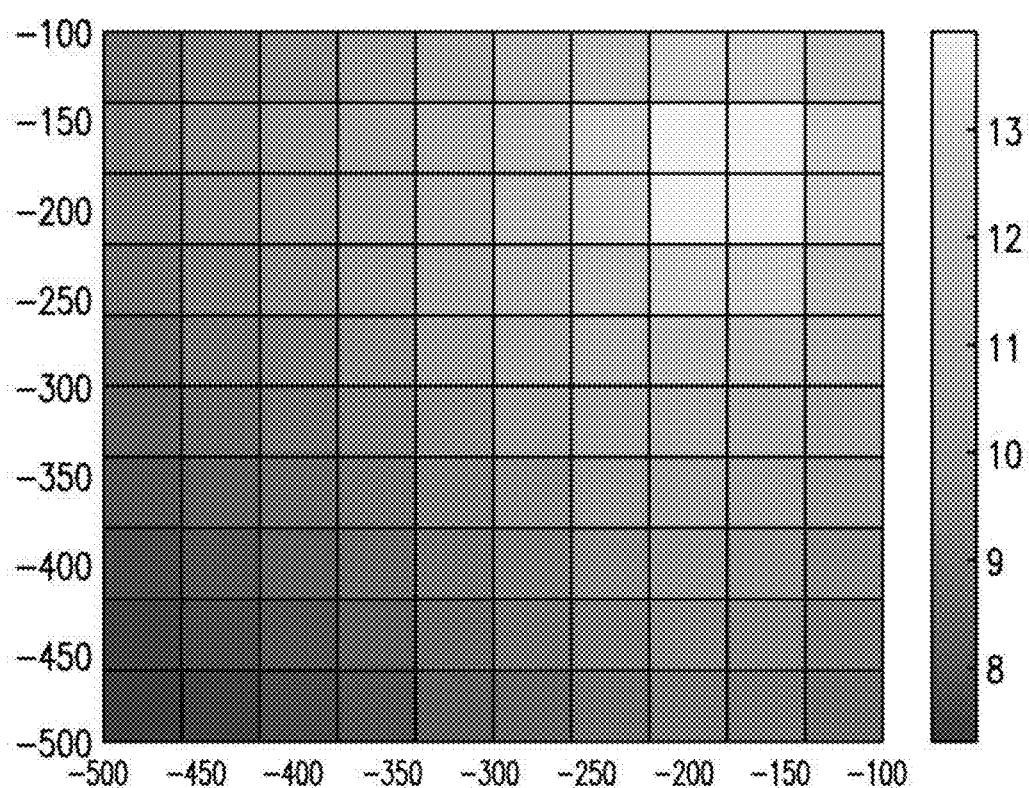
FIG. 7 illustrates a graphical representation of tool orientation error according to an embodiment of the present disclosure.

In various embodiments, for each point along the discretized trajectory, a desired orientation of the tool is determined. In various embodiments, the desired orientation is compared to one or more possible orientations. In various embodiments, the one or more possible orientations may be the actual orientation of the tool. In various embodiments, the actual orientation is compared to the desired orientation at each discretized point using equation 1 above to determine error for each discretized point along the trajectory. In various embodiments, the error for a trajectory performed from a given incision location may be visualized as shown in FIGS. 6A, 6B, and 7.

In various embodiments, a tool orientation is selected from the one or more possible orientations having the lowest error when compared to the desired orientation. In various embodiments when one of the possible orientations includes the desired orientation, that orientation is selected. In various embodiments, when the desired orientation is included among the possible orientations, the error may be zero.

In various embodiments, the determined error at each discretized point may be summed to determine a total error metric for the entire trajectory given a particular candidate incision location. In various embodiments, the total error metric may be computed for each of a plurality of candidate incision locations.

In various embodiments, the trajectory and/or total error metric may depend on the type of surgical subtasks (e.g., suturing), type of surgery, design of surgery, dimension of the instrument and/or tool (e.g., 4 DOF, 5 DOF, 6 DOF), surgical complexity, and/or circumstances (e.g., surrounding nerves that should be avoided).

In various embodiments, the plurality of candidate incision locations may collectively define a mesh. In various embodiments, the mesh may include discretized points along a surface of an anatomical model as described in more detail below with respect to FIGS. 5A and 5B.

In various embodiments, one incision point having the smallest total error metric is selected among the candidate incision points. In various embodiments, the selected incision point is presented to the user (e.g., a surgeon). In various embodiments, two or more incision points may be highlighted when the two or more incision points have the same, smallest total error metric. In various embodiments, the two or more highlighted incision points may be displayed to a user (e.g., a surgeon). In various embodiments, the user (e.g., surgeon) may determine which of the two or more highlighted incision points the surgery will ultimately use. In various embodiments, the system may receive user input selecting one of the two or more highlighted incision sites that will be used for the surgical procedure.

In various embodiments, the process described herein may be a two-phase optimization which includes incision placement and robotic base placement. In various embodiments, a user (e.g., a surgeon) may select from a finite set of incision options (e.g., informed/guided decision making). In various embodiments, the process may determine a location for the base of the robot such that the instrument tool tip is capable of reaching the surgical target. In various embodiments, the process of determining the placement of the robot base is independent from the incision placement.

In various embodiments, the process may include intraoperative optimization. In various embodiments, the incision site has already been selected and created on the patient's body. In various embodiments, a trocar has been inserted into the incision site. In various embodiments, the robot base has been locked into place. In various embodiments, an algorithm intraoperatively minimizes the error between any actual and desired orientation of the surgical instrument and/or tool.

Figure 5A:
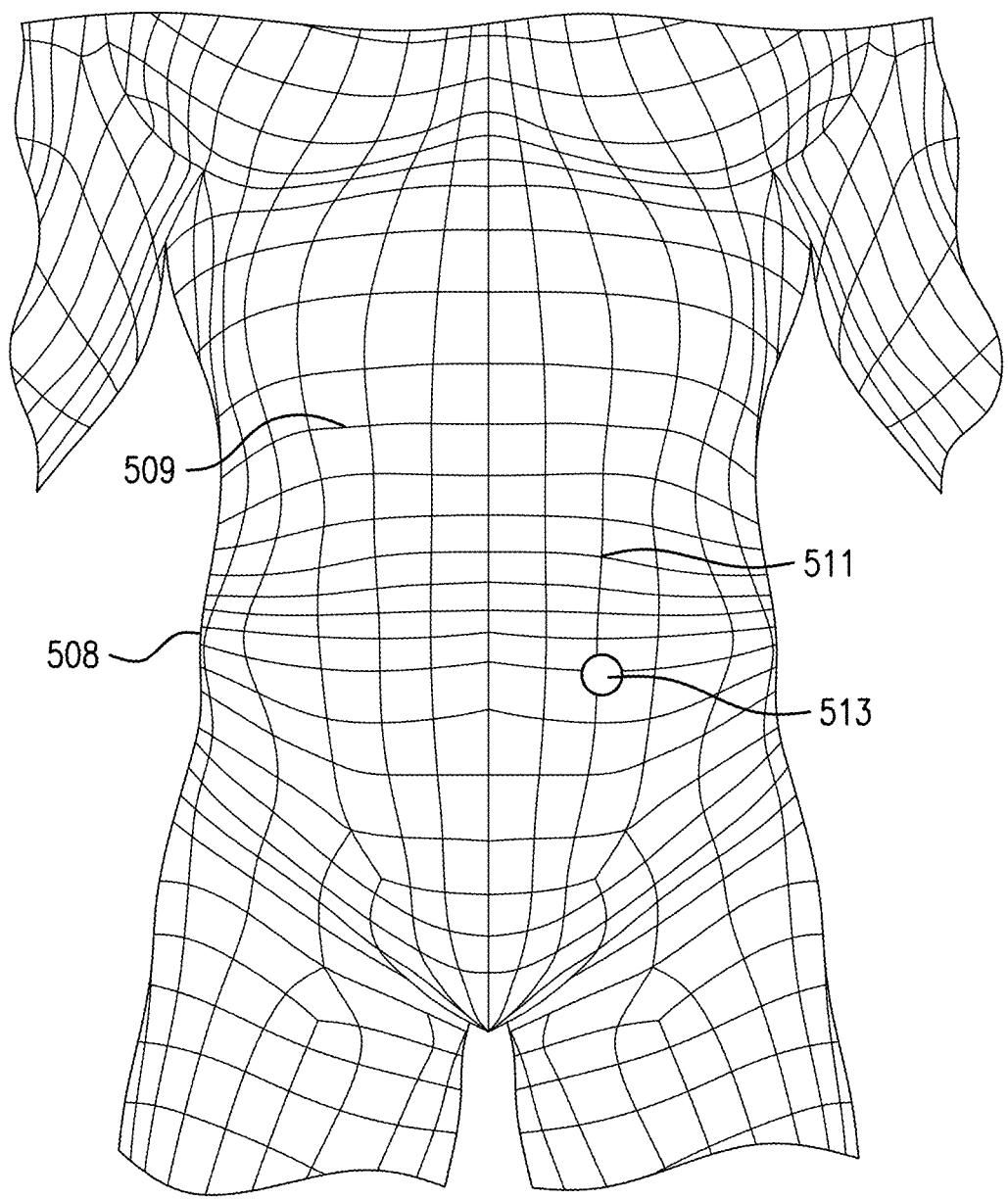
FIG. 5A illustrates a discretized anatomical model according to an embodiment of the present disclosure.

FIG. 5A illustrates a discretized anatomical model 508 according to an embodiment of the present disclosure. In various embodiments, the anatomical model may include any portion of anatomy (e.g., a complete anatomical model or only a portion of an anatomical model). In various embodiments, the anatomical model 508 is a portion of a full model and includes the human torso. In various embodiments, the anatomical model 508 may be retrieved from a generic 3D anatomical atlas. In various embodiments, the anatomical model 508 may be retrieved from patient pre-surgical imaging. In various embodiments, the anatomical model may include a three-dimensional reconstruction of the patient based on prior imaging (e.g., pre-surgical imaging). In various embodiments, one or more surfaces of the anatomical model 508 may be discretized using any suitable discretization algorithm. For example, the top surface of the anatomical model 508 may be discretized using a polygonal mesh 509 (e.g., surface mesh). In various embodiments, the mesh 509 may include a plurality of vertices 511. A vertex (or vertices), as used herein, may be any intersection point of two edges in a grid used to discretize a surface into a plurality of discrete segments (i.e., a mesh). In various embodiments, each vertex 511 may represent a potential incision site for a minimally invasive surgical procedure. In various embodiments, one or more computations may be carried out at each vertex. In various embodiments, the computation(s) may be iterated based on the results of adjacent vertices. In various embodiments, the computation(s) may be iterated until the results converge to a result (e.g., the result does not change by more than a predetermined percent from iteration to iteration). In various embodiments, an incision (and trocar) placement algorithm to optimize a surgical robot workspace may be computed at each of the vertices 511. In various embodiments, one or more error-minimizing incision site 513 may be displayed on the 3D anatomical model 508. In various embodiments, one or more error-minimizing incision site 513 may be projected onto the patient (e.g., while on the surgical table) via a projector.

In various embodiments, each vertex comprises a three-dimensional point. In various embodiments, each vertex may be located on any suitable surface of the body where a candidate incision may be placed. In various embodiments, predetermined areas of the body may be excluded from the mesh, for example, where no suitable incision can be made.

In various embodiments, the mesh 509 may be projected onto the patient via a projector. In various embodiments, the projected mesh may be, for example, a Cartesian grid. In various embodiments, a camera may record an image of the patient and the projected mesh 509. In various embodiments, the system may register the image of the patient with 3D anatomy (e.g., an anatomical atlas). In various embodiments, the system may determine the available workspace and/or tool orientation error at each of the vertices 511 of the mesh 509 for the tool to reach a particular location and/or anatomical structure within the 3D anatomy.

Figure 5B:
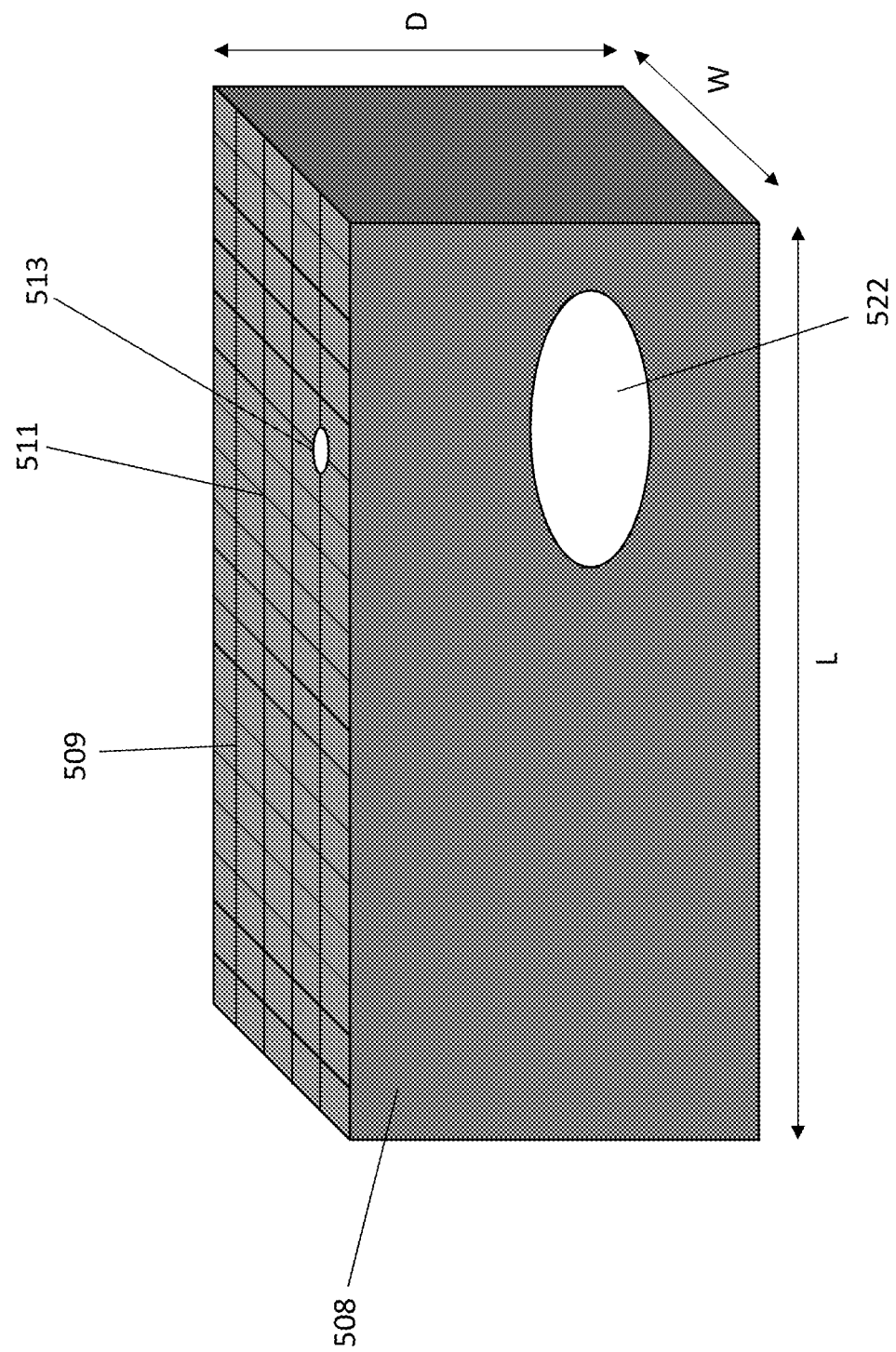
FIG. 5B illustrates a discretized anatomical model according to an embodiment of the present disclosure.

FIG. 5B illustrates a discretized anatomical model 508 according to an embodiment of the present disclosure. In various embodiments, an anatomical region of a patient having a complex shape may be represented by a simpler shape. In various embodiments, the anatomical model 508 is a simple three-dimensional shape, e.g., a rectangular box, a cube, a sphere, an ellipsoid, a cylinder, etc. For example, an abdomen of a patient may be represented as a box having a length (L), a width (W), and a depth (D). In various embodiments, one or more surfaces of the box may be discretized using any suitable discretization algorithm. For example, the top surface of the box may be discretized using a polygonal (e.g., rectangular, square, triangular, etc.) mesh 509 (e.g., surface mesh). In various embodiments, the mesh 509 may include a plurality of vertices 511. In various embodiments, each vertex 511 may represent a potential incision site for a minimally invasive surgical procedure. In various embodiments, one or more computations may be carried out at each vertex 511. In various embodiments, the computation(s) may be iterated based on the results of adjacent vertices 511. In various embodiments, the computation(s) may be iterated until the results converge to a result (e.g., the result does not change by more than a predetermined percent from iteration to iteration). In various embodiments, an incision (and trocar) placement algorithm to optimize a surgical robot workspace may be computed at each of the vertices 511. In various embodiments, although the surface of the box is 2D, an incision may be 3D. In various embodiments, all points along the incision may have the same depth (e.g., z-value) if the box is aligned with the base of the robot.

In various embodiments, a surgical path may be determined for each vertex 511 in the mesh 509. In various embodiments, an error metric may be determined for each vertex in the mesh 509. In various embodiments, a plot (e.g., surface plot) of the error metric may be displayed to a user (e.g., a surgeon) separately from the model 508. In various embodiments, a plot (e.g., surface plot) may be overlaid on the model 508. In various embodiments, the plot may be color coded with a range of colors such that one color (e.g., blue) represents the lowest or negligible determined error while another color (e.g., red) represents the highest determined error. In various embodiments, the system may provide an indication to the user (e.g., surgeon) of the error-minimizing incision point(s) for a particular surgery. In various embodiments, more than one incision point may be returned as error-minimizing for performing a particular surgery.

Similar to FIG. 5A, an error-minimizing incision site 513 (to access target anatomical structure 522 within the volume of the anatomical model 508) may be selected after tool orientation error has been determined at each vertex 511 of the mesh 509. In various embodiments, the target anatomical structure 522 may be represented by one or more point in three-dimensional space (x, y, z). In various embodiments, the point in three-dimensional space may correspond to any suitable part of the anatomical structure 522. For example the point may correspond to a centroid. In another example, the one or more point may correspond to any discrete point along the surface of the anatomical structure 522. In various embodiments, the one or more point may correspond to any discrete point within the volume of the anatomical structure 522. In various embodiments, the target anatomical structure 522 may be modeled (i.e., shape and/or position within the anatomical model 508) from a generic 3D anatomical atlas. In various embodiments, the target anatomical structure 522 may be modeled (i.e., shape and/or position within the anatomical model 508) as a 3D reconstruction of patient imaging (e.g., pre-surgical imaging). In various embodiments, the target anatomical structure may be represented as a simplified shape (e.g., a rectangular box, a cube, a sphere, an ellipsoid, a cylinder, etc.). For example, target anatomical structure 508 may be a kidney represented as an ellipsoid. In some embodiments, iterative optimization techniques are applied to select the error-minimizing incision site.

FIGS. 6A-6B illustrate graphical representations of tool orientation error according to an embodiment of the present disclosure. To generate the graphs, a desired orientation for the tool distal-most tip is provided and X and Y values for the tool were incremented by a predetermined value. For each increment, the algorithm described above was performed to compute tool orientation error. The error-minimizing orientation has the smallest amount of error between the given orientation and desired orientation. The computed errors may be visualized in graphical form. FIG. 6A represents a first incision position using the first keyhole incision as described above and shows that tool orientation error is the highest in the center of the abdomen model. FIG. 6B shows the error calculation of FIG. 6A with a refined (i.e., higher resolution) mesh.

In various embodiments, a surgeon may be provided with a map of tool error. In various embodiments, the visualized error is representative of error caused by kinematic constraints of performing a task. In various embodiments, the surgeon may be provided with two or more recommended incision sites along with the map of tool error for a particular procedure (i.e., trajectory). In various embodiments, the recommended incision sites may include those with the lowest error. In various embodiments, the recommended incision sites may include the incision site with the absolute lowest error. In various embodiments, the recommended incision sites may include the incision sites having the lowest 5%, 10%, 15%, 20%, 25%, 30%, 35%, 40%, etc. of error.

In various embodiments, if an incision site is pre-selected, the pre-operative algorithm where robot base location is pre-selected and incision site is pre-selected may not be needed. In various embodiments, the intraoperative algorithm may minimize the error at the tool tip based on the pre-selected kinematic constraints, FIG. 7 illustrates a graphical representation of tool orientation error according to an embodiment of the present disclosure. FIG. 7 represents a second incision position using the second keyhole incision as described above and shows that tool orientation error is the highest in the top-right corner of the abdomen model.

Based on the above graphs shown in FIGS. 6A, 6B and 7, the error distribution varies depending on the incision location. While these experiments were performed with a single orientation, certain surgical maneuvers (e.g., suturing) require multiple orientations through any combination of, e.g., rotations and/or translations of the surgical instrument and/or tool. Therefore, the error-minimizing incision placement requires knowledge about the procedure (how many points and in which directions). For a suturing example, if a suitable suturing procedure is known, error-minimizing incision placement may be determined from the known motions for performing the particular suture procedure.

Figure 8:
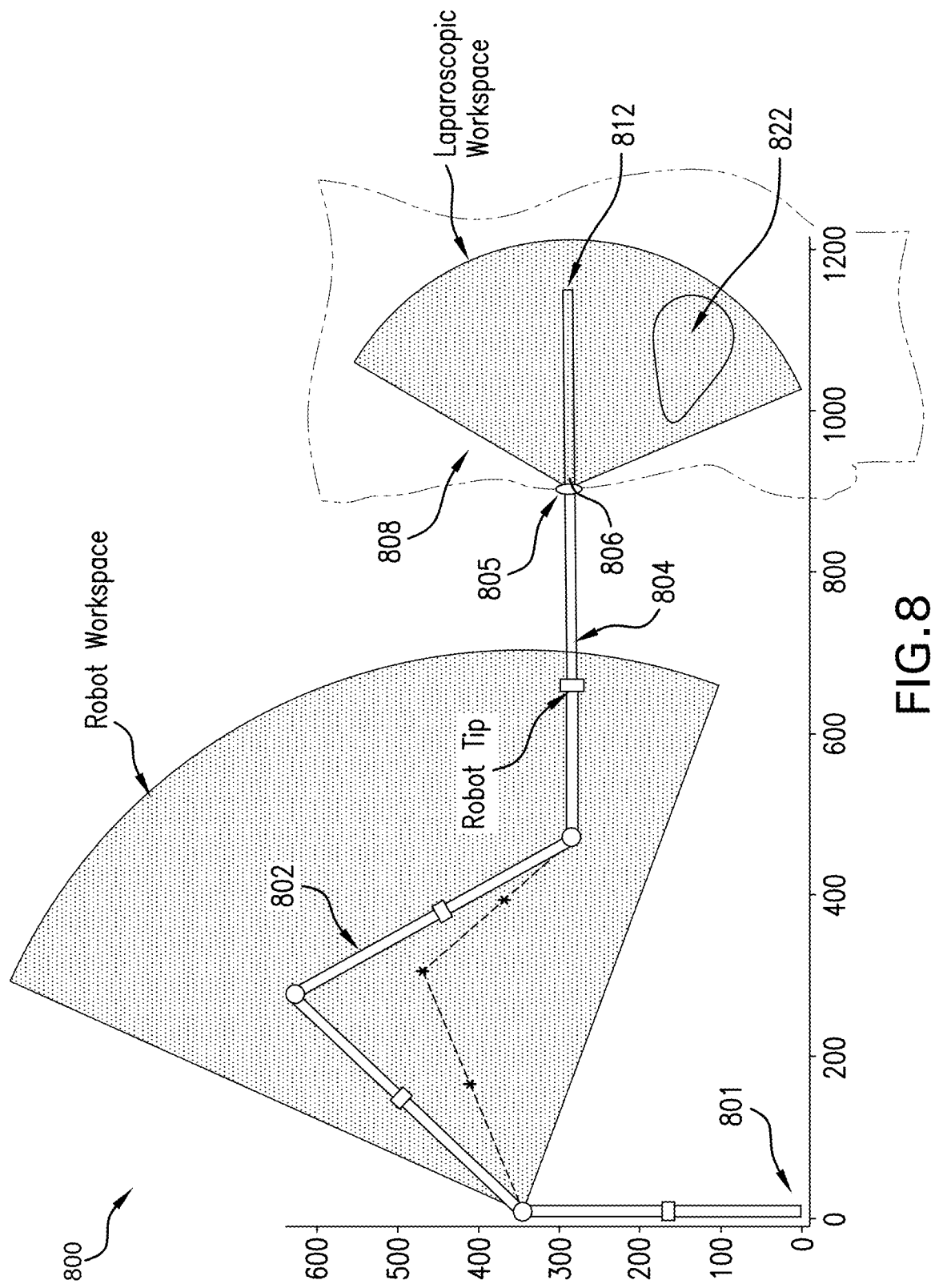
FIG. 8 illustrates a diagram of a robotic surgical system according to an embodiment of the present disclosure.

FIG. 8 illustrates a diagram of a robotic surgical system 800 according to an embodiment of the present disclosure. The robotic surgical system 800 is similar to the systems described above in that the system 800 includes a robotic arm 802 affixed to a base 801. The robotic arm 802 includes a surgical instrument 804 disposed at a distal end of the robotic arm 802. The surgical instrument 804 is inserted through a trocar 805 placed within an incision 806 and includes a tool at a distal-most end 812.

In some embodiments, iterative optimization techniques are applied to select an error-minimizing incision point, an error-minimizing trocar position, and an error-minimizing base position such that tool orientation error is minimized. In some such embodiments, an exhaustive search is performed of one or more position variable. For example, for a given base position, error may be computed for every point on a predetermined grid of potential incision points. Once the computation has been performed for each potential position for a given variable, the lowest error configuration is selected. In some embodiments, mathematical optimization methods are used, thereby avoiding an exhaustive search. For example, gradient descent may be applied to arrive at an error minimizing selection of positional variables. It will be appreciated that a variety of mathematical optimization methods are useful for minimizing error based on placement variables, e.g., differential evolution, local search, gradient descent, or simulated annealing.

In various embodiments, in a first step, an error-minimizing incision position may be selected on the patient to provide the error-minimizing amount of workspace to access one or more target anatomical structures 822 within a body cavity (e.g., abdominal cavity) of an anatomical model 808.

In various embodiments, in a second step, a position of a base 801 of the robotic arm 802 is determined. In various embodiments, the position of the base 801 is determined based on the selected error-minimizing incision site 806 from the first step. In various embodiments, the position of the base may include two or more potential error-minimizing positions that allow for optimal laparoscopic workspace for a particular surgical procedure.

In various embodiments, to determine a location of a base of a surgical robot, the surgical trajectory, surgical target (e.g., target anatomy), and instrument type are given. In various embodiments, an incision site may be selected prior to determining the location of the base.

In various embodiments, to determine the location of the base, a pre-determined space outside the patient may discretized into a grid of points, where each point is candidate location for the base. For a candidate location of a base 801 and the incision site 806, reachability of the robot arm and/or tool may be determined. In various embodiments, the reachability may be constrained to a region defined by an arc, as shown in FIG. 8. In various embodiments, moving the base changes the shape and/or volume of the workspace. For a candidate base 801 (and pre-selected incision site 806), an error metric may be determined. In various embodiments, the error metric may be based on the trajectory of the tool, similar to the error determination described above. In various embodiments, the trajectory of the tool is discretized and an error is determined for the candidate base location. In various embodiments, as an example, one or more locations of the base may have the similar (e.g., same) error as computed for the tool by itself where the robot workspace is capable of performing the trajectory (e.g., with minimal error between the actual and desired orientation). In various embodiments, if the robot base is located too far away from the patient, for example, the tool orientation may significantly differ from the desired tool orientation because the robot is not capable of assuming an error-minimizing tool orientation given the constraint of the incision site (and trocar).

In various embodiments, one or more of the discretized locations may be excluded. In various embodiments, the excluded location(s) may correspond to location(s) that are unavailable for positioning the robotic base. For example, required healthcare equipment (e.g., an anesthesia monitor/delivery device) may be located near the patient.

In various embodiments, the candidate base location(s) with the least error are recommended for the robot placement. In various embodiments, a map of error may be provided to the user with recommended base location(s) for the surgical robot.

In various embodiments, in a third step, tool orientation error is determined as described above. In various embodiments, tool orientation error may be minimized to avoid one or more objects within the laparoscopic workspace (e.g., critical nerves and/or blood vessels). In various embodiments, for example, a tool has a desired orientation and a cone extending therefrom representing possible orientations. In various embodiments, one orientation in the cone will minimize the error as defined in equation 1. In various embodiments, if the cone of possible orientations includes the desired orientation, the error is zero.

In various embodiments, the tool orientation error may be determined as the difference between an actual trajectory and a desired trajectory of pathing of the distal-most end of the tool.

Figure 9:
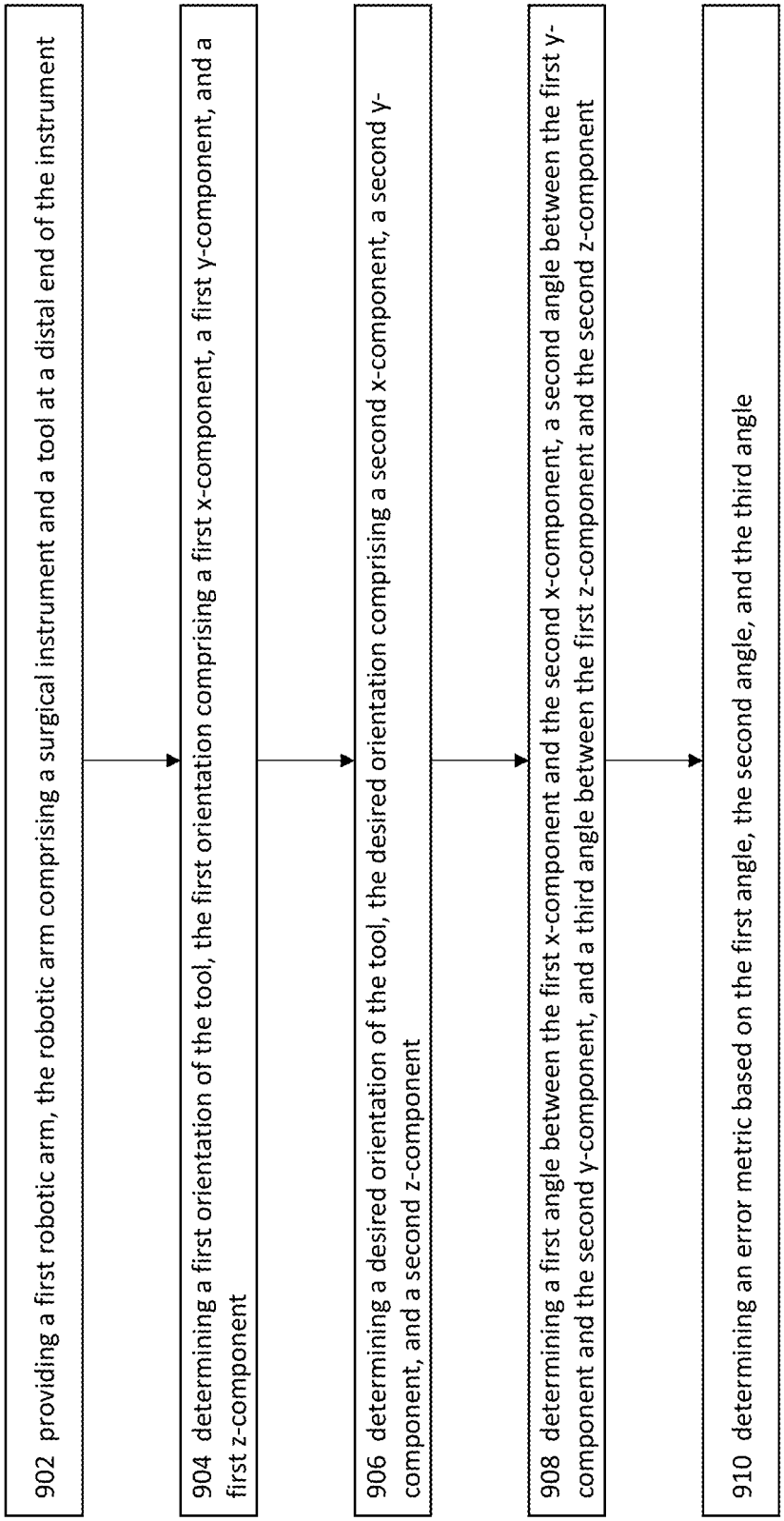
FIG. 9 illustrates a flowchart of a method for computing tool error according to an embodiment of the present disclosure.

FIG. 9 illustrates a flowchart of a method 900 for computing end effector error according to an embodiment of the present disclosure. At 902, a first robotic arm is provided where the robotic arm includes a trocar and an end effector. At 904, a first orientation of the end effector is determined. The first orientation includes a first x-component, a first y-component, and a first z-component. At 906, a desired orientation of the end effector is determined, the desired orientation comprising a second x-component, a second y-component, and a second z-component. At 908, a first angle between the first x-component and the second x-component is determined, a second angle between the first y-component and the second y-component is determined, and a third angle between the first z-component and the second z-component is determined. At 910, an error metric based on the first angle, the second angle, and the third angle is determined.

In various embodiments, determining an error metric may include summing the squares of each of the first angle, the second angle, and the third angle. In various embodiments, two or more error metrics may be determined, such that each error metric corresponds to a different trocar position. In various embodiments, the determined error metrics for each trocar position may be compared to determine an error-minimizing trocar position for a particular surgical procedure.

In various embodiments, the algorithm inputs for determining end effector orientation error may include, for example, trocar position, abdominal cavity size and position, and desired end effector tip orientation. In various embodiments, error in the end effector orientation may be determined for two or more potential incision sites and the errors may be compared to determine an error-minimizing incision site for a particular surgical procedure.

Figure 10:
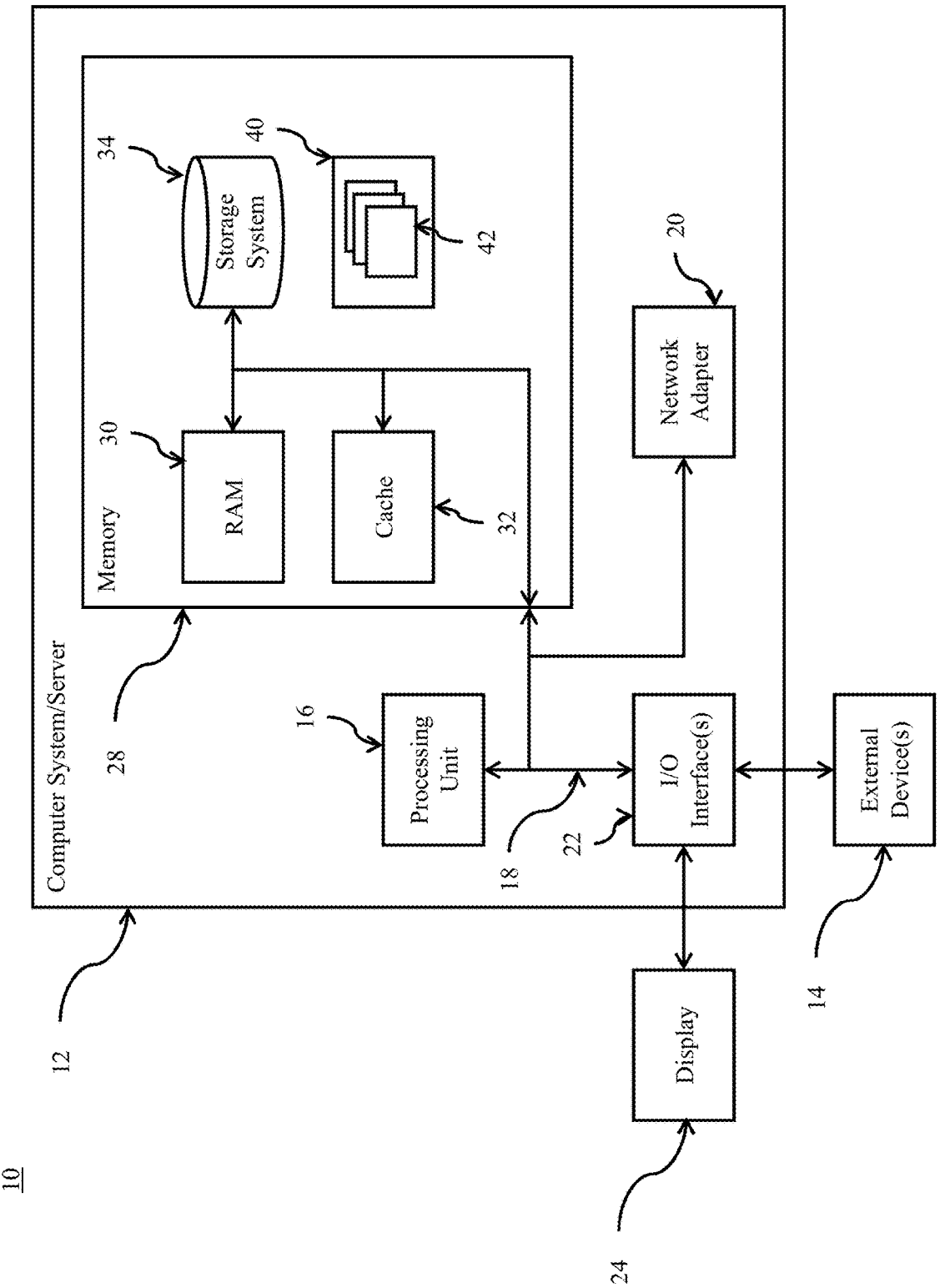
FIG. 10 depicts an exemplary computing node according to various embodiments of the present disclosure.

Referring now to FIG. 10, a schematic of an exemplary computing node is shown that may be used with the computer vision systems described herein. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 10, computer system/server 12 in computing node 10 is shown in the form of a general-purpose computing device. The components of computer system/server 12 may include, but are not limited to, one or more processors or processing units 16, a system memory 28, and a bus 18 coupling various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

In other embodiments, the computer system/server may be connected to one or more cameras (e.g., digital cameras, light-field cameras) or other imaging/sensing devices (e.g., infrared cameras or sensors).

The present disclosure includes a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD- ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In various embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In various alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   (a) providing (i) a robotic arm having a proximal end and a distal end, wherein the proximal end is fixed or coupled to a base and (ii) a surgical tool disposed on or attached to the distal end of the robotic arm;
   (b) determining one or more trajectories to move the surgical tool towards one or more anatomical structures of a patient, wherein the one or more trajectories are discretized into a plurality of points;
   (c) determining (i) one or more error-minimizing incision sites on the patient and (ii) one or more tool orientation errors associated with the surgical tool for each of the plurality of points along the one or more trajectories, based at least in part on a location of the one or more anatomical structures; and (d) adjusting a movement of the robotic arm or the surgical tool based on a total error metric associated with the one or more trajectories, wherein the total error metric includes a summation of the one or more tool orientation errors determined for each of the plurality of points along the one or more trajectories, and wherein the one or more trajectories correspond to an error-minimizing incision site having a total error metric that is less than a total error metric for one or more other error-minimizing incision sites.

2. The method of claim 1, wherein in (c), the one or more error-minimizing incision sites comprise a plurality of candidate incision sites selectable by a user supervising, controlling, or operating the robotic arm, wherein each of the plurality of candidate incision sites includes a respective total error metric.

3. The method of claim 1, wherein in (c), the one or more tool orientation errors are determined based at least in part on (a) an angle between a desired x-component and an actual x-component of the surgical tool, (b) an angle between a desired y-component and an actual y-component of the surgical tool, and (c) an angle between a desired z-component and an actual z-component of the surgical tool.

4. The method of claim 1, wherein (c) further comprises discretizing a surface of an anatomical model of the patient into a plurality of regions, wherein the one or more error-minimizing incision sites correspond to at least a subset of the plurality of regions on the discretized surface.

5. The method of claim 4, wherein the anatomical model comprises an anatomical atlas.

6. The method of claim 4, wherein the anatomical model comprises a three-dimensional reconstruction of patient anatomy based on one or more images of the patient.

7. The method of claim 1, further comprising, subsequent to (c), determining an error minimizing position of the base to which the robotic arm is fixed or coupled, wherein the error-minimizing position is determined based at least in part on the error-minimizing incision site selected by a user.

8. The method of claim 7, wherein determining the error-minimizing position of the base comprises discretizing a space exterior to the patient into a plurality of candidate base locations.

9. The method of claim 8, further comprising, for each of the plurality of candidate base locations, determining a second tool orientation error based on the one or more discretized trajectories, wherein the second tool orientation error is determined based on (a) an angle between a desired x-component and an actual x-component of the surgical tool, (b) an angle between a desired y-component and an actual y-component of the surgical tool, and (c) an angle between a desired z-component and an actual z-component of the surgical tool.

10. The method of claim 9, wherein (d) further comprises adjusting a position or an orientation of the base based on the second tool orientation error.

11. The method of claim 1, wherein the one or more trajectories are determined based at least in part on a type of surgical task, a type of surgery, a dimension of the surgical tool, or a number of degrees of freedom of the robotic arm or the surgical tool.

12. The method of claim 1, wherein the one or more trajectories are determined based at least in part on one or more regions to avoid during a surgical procedure.

13. The method of claim 1, wherein the total error metric is determined based at least in part on a type of surgical task, a type of surgery, a dimension of the surgical tool, or a number of degrees of freedom of the robotic arm or the surgical tool.

14. The method of claim 1, wherein the total error metric is determined based at least in part on one or more regions to avoid during a surgical procedure.

15. The method of claim 1, further comprising, subsequent to (c), projecting the one or more error-minimizing incision sites onto the patient using a projector.

16. A method comprising:
(a) providing (i) a robotic arm having a proximal end and a distal end, wherein the proximal end is fixed or coupled to a base and (ii) a surgical tool disposed on or attached to the distal end of the robotic arm;
(b) determining one or more trajectories to move the surgical tool towards one or more anatomical structures of a patient, wherein the one or more trajectories are discretized into a plurality of points;
(c) determining (i) one or more error-minimizing incision sites on the patient and (ii) one or more tool orientation errors associated with the surgical tool for each of the plurality of points along the one or more trajectories, based at least in part on a location of the one or more anatomical structures;
(d) generating a plot of a total error metric for each of the one or more error-minimizing incision sites, and
(e) adjusting a movement of the robotic arm of the surgical tool based on a total error metric associated with the one or more trajectories, wherein the total error metric includes a summation of the one or more tool orientation errors determined for each of the plurality of points along the or more trajectories.

17. The method of claim 16, wherein the plot comprises a color coded indication for each of the one or more error-minimizing incision sites based on a magnitude of the total error metric associated with the one or more error-minimizing incision sites.

18. The method of claim 16, further comprising overlaying the plot of the total error metric for each of the one or more error-minimizing incision sites onto an anatomical model of the patient.

19. A system comprising:
a robotic arm having a proximal end and a distal end, wherein the proximal end is fixed or coupled to a base;
a surgical tool disposed on or attached to the distal end of the robotic arm; and
a computing node including a processor and a computer readable storage medium having program instructions executable by a processor to:
(a) determine one or more trajectories to move the surgical tool towards one or more anatomical structures of a patient, wherein the one or more trajectories are discretized into a plurality of points;
(b) determine (i) one or more error-minimizing incision sites on the patient and (ii) one or more tool orientation errors associated with the surgical tool for each of the plurality of points along the one or more trajectories, based at least in part on a location of the one or more anatomical structures; and
(c) adjust a movement of the robotic arm or the surgical tool based on a total error metric associated with the one or more trajectories, wherein the total error metric includes a summation of the one or more tool orientation errors determined for each of the plurality of points along the one or more trajectories, wherein the one or more trajectories correspond to an error-minimizing incision site having a total error metric that is less than a total error metric for one or more other error-minimizing incision sites, and wherein the total error metric for a selected incision site is iteratively computed based on one or more error metrics associated with one or more candidate incision sites adjacent to the selected incision site.

20. The system of claim 19, wherein in (b), the one or more tool orientation errors are determined based at least in part on a location of the one or more error-minimizing incision sites.

21. The system of claim 19, wherein in (c), the program instructions executable by the processor to adjust the movement of the robotic arm or the surgical tool comprises one or more rotations or translations.

* * * * *